United States Patent [19]

Cumming

[11] Patent Number: 5,496,366
[45] Date of Patent: Mar. 5, 1996

[54] ACCOMMODATING INTRAOCULAR LENS

[76] Inventor: J. Stuart Cumming, 1211 W. LaPalma Ave., Anaheim, Calif. 92801

[21] Appl. No.: 255,356

[22] Filed: Jun. 7, 1994

Related U.S. Application Data

[60] Division of Ser. No. 20,630, Feb. 22, 1993, abandoned, which is a continuation-in-part of Ser. No. 915,453, Jul. 16, 1992, abandoned, which is a continuation-in-part of Ser. No. 515,636, Apr. 27, 1990, abandoned.

[51] Int. Cl.$^6$ ..................................................... A61F 2/16
[52] U.S. Cl. .............................................................. 623/6
[58] Field of Search ................................. 623/6; 606/107

[56] References Cited

U.S. PATENT DOCUMENTS 5,047,051  9/1991  Cumming .................................. 623/6

FOREIGN PATENT DOCUMENTS 0336877  10/1989  European Pat. Off. .

*Primary Examiner*—Randy C. Shay
*Attorney, Agent, or Firm*—Boniard I. Brown

[57] ABSTRACT

An accommodating intraocular lens to be implanted within the natural capsular bag of a human eye from which the natural lens matrix has been removed through an anterior capsulotomy in the bag circumferentially surrounded by a capsular remnant. During a postoperative healing period following surgery, the anterior capsular remnant fuses to the posterior capsule of the bag by fibrosis about haptics on the implanted lens, and the lens is deflected rearwardly to a distant vision position against the elastic posterior capsule of the bag in which the posterior capsule is stretched rearwardly. After fibrosis is complete, natural brain-induced contraction and relaxation of the ciliary muscle relaxes and stretches the fused remnant and increases and reduces vitreous pressure in the eye to effect vision accommodation by the fused remnant, the posterior capsule, and vitreous pressure. A method of utilizing the intraocular lens in a human eye to provide the eye with accommodation and to enable utilization of a lens with a relatively large optic.

26 Claims, 13 Drawing Sheets

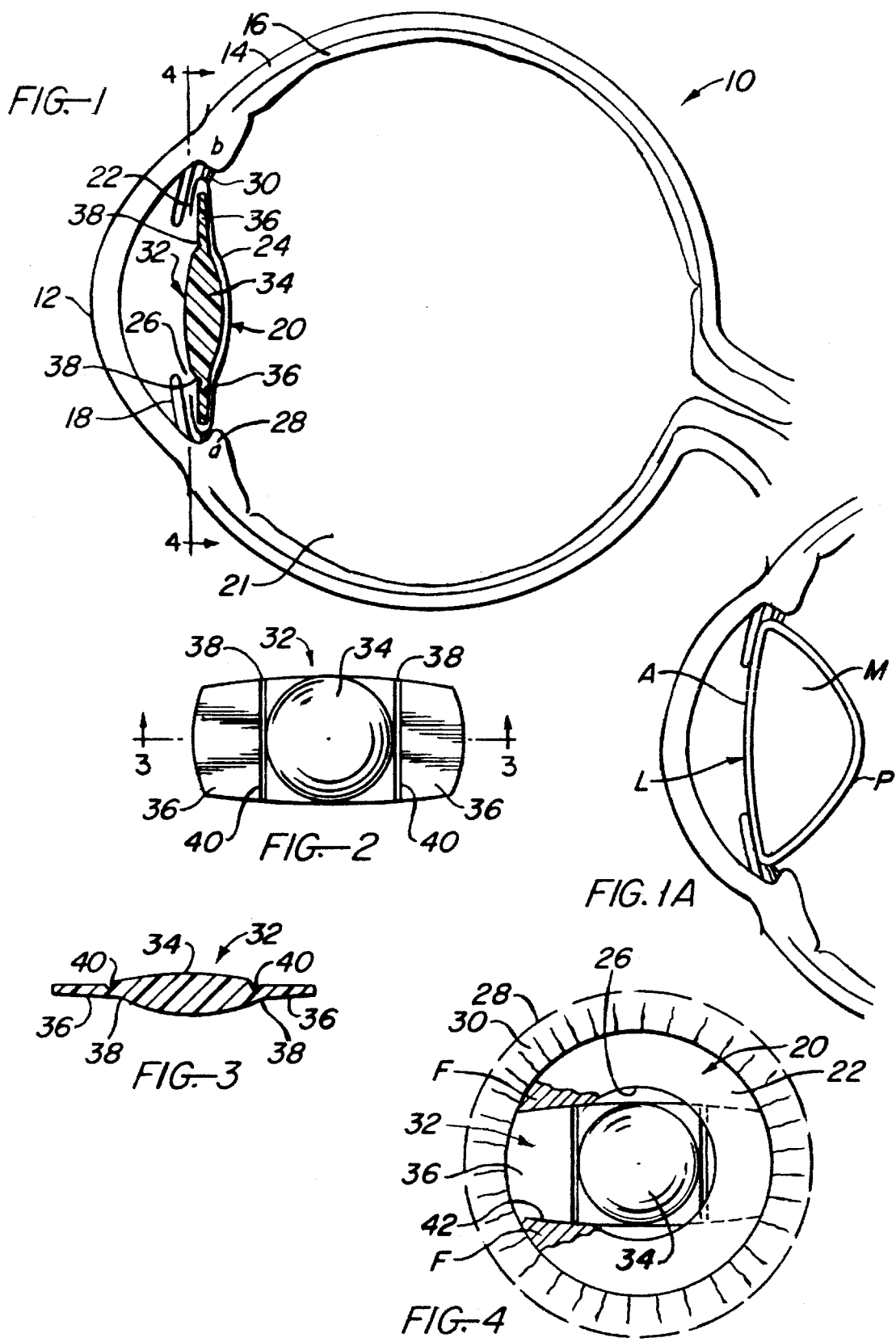

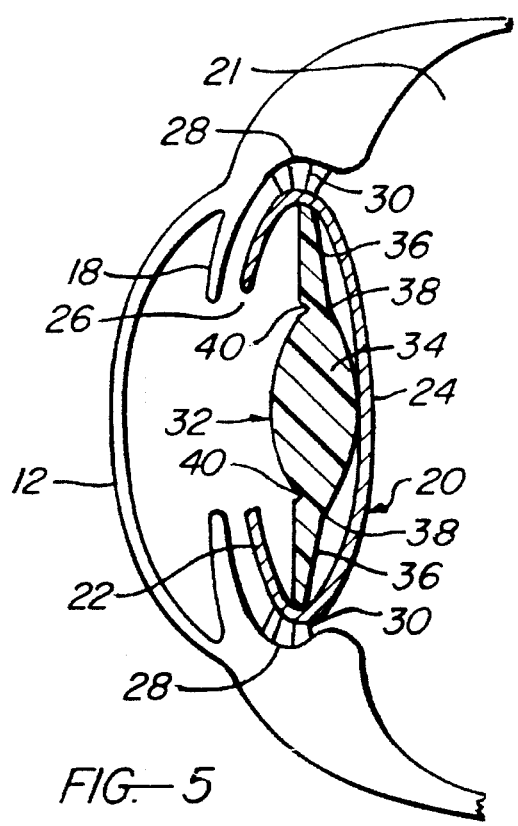
FIG.—5
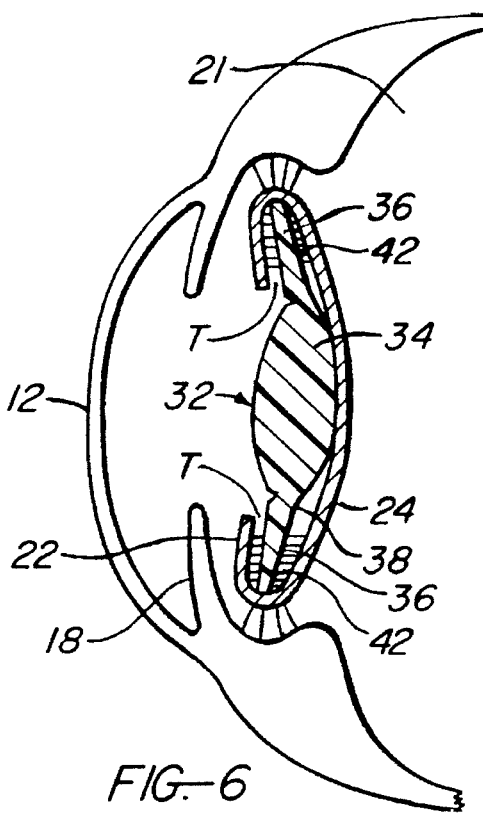
FIG.—6
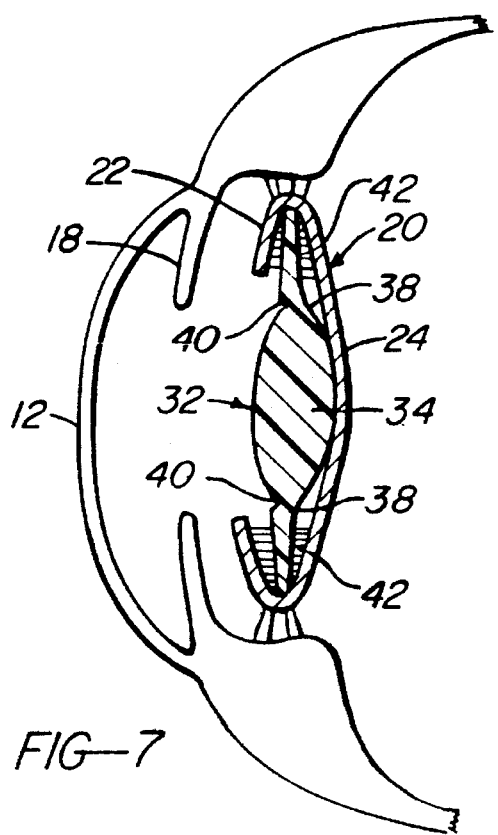
FIG.—7
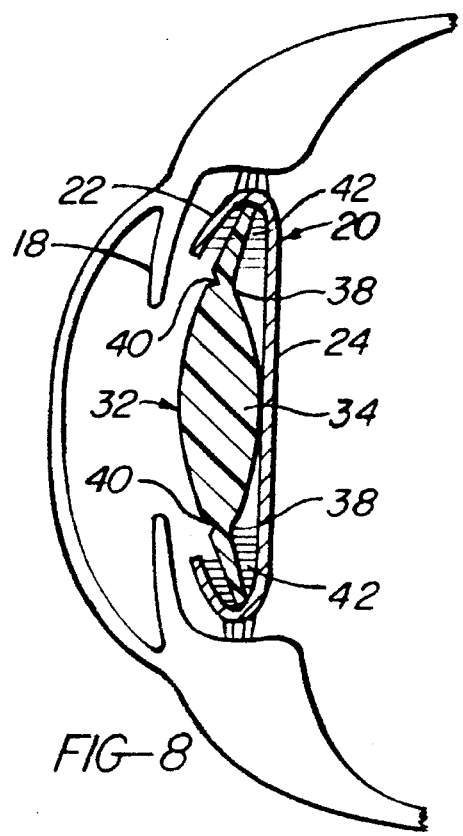
FIG.—8

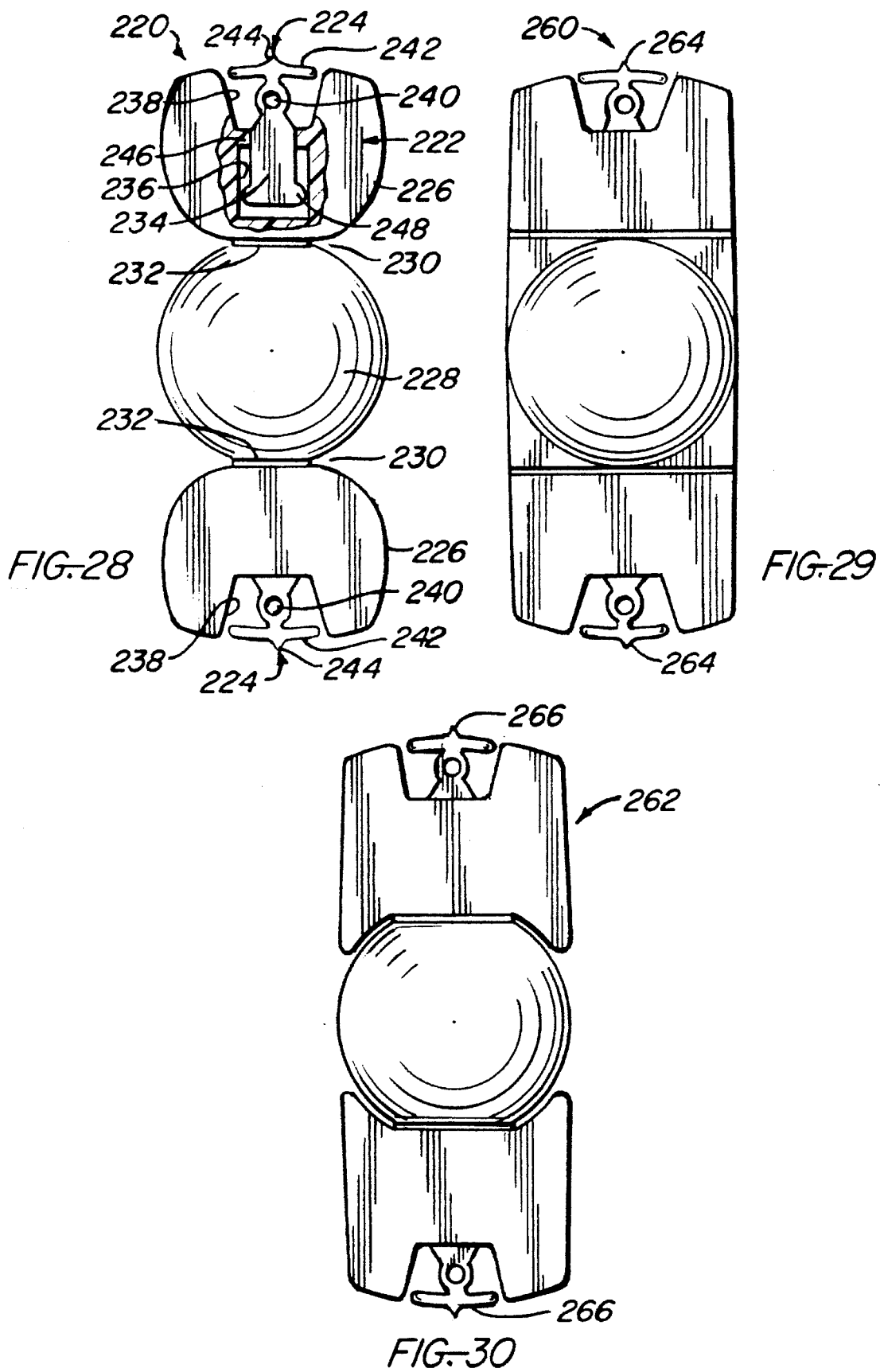

ACCOMMODATING INTRAOCULAR LENS

This application is a divisional of application Ser. No. 08/020,630, filed Feb. 26, 1992, now allowed, which is a continuation-in-part of application Ser. No. 07/915,453, filed Jul. 16, 1992, now abandoned, which, in turn, is a continuation-in-part of my application Ser. No. 07/515,636, filed Apr. 27, 1990, now abandoned. Reference is also made to my copending application Ser. No. 07/744,472 filed Aug. 12, 1991.

BACKGROUND OF THE INVENTION

FIELD OF THE INVENTION

This invention relates generally to intraocular lenses and more particularly to novel accommodating intraocular lenses for implantation within the capsular bag of a human eye from which the natural lens matrix has been removed by an extraction procedure which leaves intact within the eye the posterior capsule and an anterior capsule remnant of the natural lens. The invention relates also to a novel method of utilizing the intraocular lenses in a human eye to provide the patient with accommodation capability responsive to normal ciliary muscle action.

PRIOR ART

The human eye has an anterior chamber between the cornea and the iris, a posterior chamber behind the iris containing a crystalline lens, a vitreous chamber behind the is containing vitreous humor, and a retina at the rear of the vitreous chamber. The crystalline lens of a normal human eye has a lens capsule attached about its periphery to the ciliary muscle of the eye by zonules and containing a crystal line lens matrix. This lens capsule has elastic optically clear anterior and posterior membrane-like walls commonly referred by ophthalmologists as anterior and posterior capsules, respectively. Between the iris and ciliary muscle is an annular crevice-like space called the ciliary sulcus.

The human eye possesses natural accommodation capability. Natural accommodation involves relaxation and constriction of the ciliary muscle by the brain to provide the eye with near and distant vision. This ciliary muscle action is automatic and shapes the natural crystalline lens to the appropriate optical configuration for focussing on the retina the light rays entering the eye from the scene being viewed.

The human eye is subject to a variety of disorders which degrade or totally destroy the ability of the eye to function properly. One of the more common of these disorders involves progressive clouding of the natural crystalline lens matrix resulting in the formation of what is referred to as a cataract. It is now common practice to cure a cataract by surgically removing the cataractous human crystalline lens and implanting an artificial intraocular lens in the eye to replace the natural lens. The prior art is replete with a vast assortment of intraocular lenses for this purpose. Examples of such lenses are described in the following patents: U.S. Pat. Nos. 4,254,509, 4,298,996, 4,409,691, 4,424,597, 4,573,998, 4,664,666, 4,673,406, 4,738,680, 4,753,655, 4,778,463, 4,813,955, 4,840,627, 4,842,601, 4,963,148, 4,994,082, 5,047,051.

As is evident from the above patents, intraocular lenses differ widely in their physical appearance and arrangement. This invention is concerned with intraocular lenses of the kind having a central optical region or optic and haptics which extend outward from the optic and engage the interior of the eye in such a way as to support the optic on the axis of the eye. My above-listed patent U.S. Pat. No. 5,047,051, which was filed concurrently with my earlier mentioned application Ser. No. 07/515,636, discloses an intraocular lens having a haptic anchor plate, an optic at the longitudinal center of the plate, and resilient haptic loops staked to the ends of the plate.

Up until the late 1980's, cataracts were surgically removed by either intracapsular extraction involving removal of the entire human lens including both its outer lens capsule and its inner crystalline lens matrix, or by extracapsular extraction involving removal of the anterior capsule of the lens and the inner crystalline lens matrix but leaving intact the posterior capsule of the lens. Such intracapsular and extracapsular procedures are prone to certain post-operative complications which introduce undesirable risks into their utilization. Among the most serious of these complications are opacification of the posterior capsule following extracapsular lens extraction, intraocular lens decentration, cystoid macular edema, retinal detachment, and astigmatism.

Starting in the late 1980's, an improved surgical procedure called capsulorhexis was developed to alleviate or avoid the above and other post-operative complications and risks involved in intracapsular and extracapsular cataract extraction. Simply stated, capsulorhexis involves forming in he anterior capsule of the natural lens an opening called a capsulotomy. Capsulorhexis leaves intact within the eye a capsular bag having an elastic posterior capsule, an anterior capsular remnant about the anterior capsulotomy, and an annular sulcus, referred to herein as a capsular bag sulcus, between the anterior capsule remnant and the outer circumference of the posterior capsule. This capsular bag remains attached about its periphery to the surrounding ciliary muscle of the eye by the zonules of the eye. The cataractous natural lens matrix is extracted from the capsular bag through the anterior capsulotomy by phacoemulsification and aspiration or in some other way after which an intraocular lens is implanted within the bag through the capsulotomy.

The type of anterior capsulotomy known as capsulorhexis involves a continuous tear circular or round capsulotomy, tearing the anterior capsule of the natural lens capsule along a generally circular tear line substantially coaxial with the lens axis and removing the generally circular portion of the anterior capsule surrounded by the tear line. A continuous tear circular capsulorhexis, if performed properly, provides a generally circular capsulotomy through the anterior capsule of the natural lens capsule substantially coaxial with the axis of the eye and surrounded circumferentially by a continuous annular remnant or rim of the anterior capsule having a relatively smooth and continuous inner edge bounding the capsulotomy. During a continous tear circular capsulorhexis, however, the anterior rim is often accidentally torn or sliced radially or otherwise ruptured, or the inner rim edge is nicked or sliced in a manner which renders the rim prone to tearing radially when the rim is stressed, as it is during fibrosis as discussed below.

Another capsulorhexis procedure, referred to as an envelope capsulorhexis, involves cutting a horizontal incision in the anterior capsule of the natural lens capsule, then cutting two vertical incisions in the anterior capsule intersecting and rising from the horizontal incision, and finally tearing the anterior capsule along a tear line having an upper upwardly arching portion which starts at the upper extremity of the vertical incision and continues in a downward vertical portion parallel to the vertical incision which extends downwardly and then across the second vertical incision. This procedure produces in the anterior capsule a generally archway-shaped envelope capsulotomy centered on the axis of the eye. The capsulotomy is bounded at its bottom by the horizontal incision, at one vertical side by the vertical incision, at its opposite vertical side by the second vertical incision of the anterior capsule, and at its upper side by the upper arching portion of the capsule tear. The vertical incision and the adjacent end of the horizontal incision form a flexible flap at one side of the capsulotomy. The vertical tear edge and the adjacent end of the horizontal incision form a second flap at the opposite side of the capsulotomy.

Yet another capsulorhexis procedure, referred to as a beer can or can opener capsulorhexis, involves piercing the anterior capsule of the natural lens capsule at a multiplicity of intersecting positions along a circular line substantially coaxial with the axis of the eye and then removing the generally circular portion of the capsule circumferentially surrounded by the line. This procedure produces a generally circular capsulotomy substantially coaxial with the axis of the eye and bounded circumferentially by an annular remnant or rim of the anterior capsule. The inner edge of this rim has a multiplicity of scallops formed by the edges of the pierced holes in the anterior capsule which render the annular remnant or rim prone to tearing radially when the rim is stressed, as it is during fibrosis as discussed below.

Intraocular lenses also differ with respect to their accommodation capability, and their placement in the eye. Accommodation is the ability of an intraocular lens to accommodate, that is to focus the eye for near and distant vision. My copending application Ser. No. 07/744,472 and some of the earlier listed patents describe accommodating intraocular lenses. Others of the listed patents describe non-accommodating intraocular lenses. Most non-accommodating lenses have single focus optics which focus the eye at a certain fixed distance only and require the wearing of eye glasses to change the focus. Other non-accommodating lenses have bifocal optics which image both near and distant objects on the retina of the eye. The brain selects the appropriate image and suppresses the other image, so that a bifocal intraocular lens provides both near vision and distant vision sight without eyeglasses. Bifocal intraocular lenses, however, suffer from the disadvantage that each bifocal image represents only about 40% of the available light and the remaining 20% of the light is lost in scatter.

There are four possible placements of an intraocular lens within the eye. These are (a) in the anterior chamber, (b) in the posterior chamber, (c) in the capsular bag, and (d) in the vitreous chamber. The intraocular lens disclosed in my copending application Ser. No. 07/744,472 is intended for placement within the capsular bag.

SUMMARY OF THE INVENTION

According to one of its aspects, this invention provides improved plate haptic accommodating intraocular lenses to be implanted within the capsular bag of a human eye which remains in the eye after removal of the natural matrix from the human lens capsule through an anterior capsulotomy produced by a capsulorhexis procedure. An improved accommodating intraocular lens according to the invention has a central optic and two plate haptics which extend generally radially outward from diametrically opposite sides of the optic and are movable anteriorly and posteriorly relative to the optic. The width of the plate optics is substantially the same as the diameter of the optic. In some described lens embodiments, the plate haptics are relatively stiff, their inner ends are hinged to the optic, and the anterior/posterior movement of the haptics involves pivotal movement of the haptics at their hinges. In other described embodiments, the plate haptics are resiliently flexible, and the anterior/posterior movement of the haptics relative to the optic involves resilient flexing or bending of the haptics throughout their length. In this regard, it is important to note that the terms "flex", "flexing", "flexible", and the like are used herein in a broad sense to cover both hinged and resiliently bendable haptics.

Certain of the described lens embodiments, referred to as simple plate haptic lenses, are intended for use when the capsulorhexis procedure utilized in cataract surgery is a properly performed continuous tear circular capsulotomy, which provides an anterior capsulotomy circumferentially surrounded by an anterior capsule remnant in the form of an intact, circumferentially continous annular rim that remains free of splits and tears throughout fibrosis following surgery. A simple plate haptic lens of the invention is implanted within the eye in a position wherein the lens optic is aligned on the axis of the eye with the anterior capsulotomy and the outer ends of the plate haptics are situated within the capsular bag sulcus in contact with the sulcus wall. The normally posterior side of the lens then faces the elastic posterior capsule of the bag.

During a post operative healing period on the order of three weeks, active endodermal cells on the posterior side of the anterior capsular rim cause fusion of the rim to the elastic posterior capsule by fibrosis. Fibrosis occurs about the haptics in such a way that the haptics are effectively "shrink-wrapped" by the capsular bag and form radial pockets between the anterior rim and the posterior capsule. These pockets contain the haptics and act to position and center the lens in the eye. The anterior capsular rim shrinks during fibrosis. This shrinkage combined with shrink-wrapping of the haptics causes endwise compression of the lens in a manner which tends to deflect the center of the lens along the axis of the eye relative to the fixated outer haptic ends. The intact fibrosed capsular rim prevents forward deflection oft he lens, so that fibrosis-induced deflection of the lens occurs rearwardly to a position in which tile lens presses against the elastic posterior capsule and stretches this capsule rearwardly.

In order to insure proper formation of the haptic pockets during fibrosis, brain-induced flexing of the lens during fibrosis is prevented by using a ciliary muscle relaxant, such as Atropine drops, to maintain the ciliary muscle in a relaxed state and/or using a suture to physically prevent flexing of the lens. In the Atropine-induced relaxed state of the ciliary muscle, the capsular bag is stretched to its maximum diameter. The anterior capsular rim is then stretched to a taut trampoline-like condition or position in which the rim prevents forward flexing of lens from its rim posterior position against the posterior capsule. The undergoes fibrosis from this taut condition or position.

Use of the ciliary muscle relaxant is discontinued upon completion of fibrosis. Thereafter, when the brain activates the ciliary muscle to its natural relaxed state, the capsular bag and the fibrosed anterior capsular rim are stretched, the rim to its taut trampoline-like condition in which the rim deflects the lens rearwardly to and holds the lens in its posterior position. In this position of the lens, which is its distant vision position, it presses rearwardly against and stretches the elastic posterior capsule. The stretched posterior capsule then exerts a forward bias force on the lens.

The plate haptic lenses of the invention are uniquely constructed and arranged to utilize the fibrosed anterior capsular rim, the elastic posterior capsule, the vitreous cavity pressure, and the natural brain-controlled ciliary muscle action of the eye to provide postoperative accommodation for near vision. Thus, when looking at a near object, the brain constricts the ciliary muscle. This relaxes the fibrosed anterior rim, increases vitreous cavity pressure, and compresses the lens endwise in such a way as to effect forward deflection, i.e. accommodation movement, of the lens optic along the axis of the eye to a near vision position. Depending upon the amount of accommodation, accommodation deflection of the lens is produced initially by the increase in vitreous pressure and the forward bias force of the stretched posterior capsule and finally by forward buckling of the lens in response to endwise compression of the lens. Subsequent brain-activated relaxation of the ciliary muscle stretches the capsular bag and the fibrosed anterior capsular rim to return the lens rearwardly toward its distant vision position.

A plate haptic lens according to the invention may have a normal unstressed configuration, such that when deflected from this normal unstressed configuration, the lens develops internal elastic strain energy forces which bias the lens toward its normal unstressed configuration in a manner which aids accommodation. The lens may be generally flat, anteriorly arched, or posteriorly arched in this normal unstressed configuration. One disclosed embodiment of the lens includes auxiliary springs for aiding lens accommodation. Some disclosed lens embodiments have integral fixation means at the haptic ends around which fibrosis of the anterior rim of the capsular bag occurs to fix the lens against dislocation in the eye. Other disclosed embodiments have fixation elements from which the lens proper is separable to permit later removal of the lens for repair or correction and replacement of the lens in its exact original position within the eye.

The simple plate haptic lenses discussed above are intended for use when the capsulorhexis procedure performed on the eye provides an anterior capsular remnant or rim that remains intact and circumferentially continuous throughout fibrosis. According to another of its aspects, this invention provides modified accommodating intraocular lenses, referred to as plate haptic spring intraocular lenses, for use when the anterior capsular remnant or rim of the capsular bag is ruptured, that is cut or torn. A ruptured capsular rim may be produced in different ways. For example, improper performance of a continous tear circular capsulorhexis may result in accidental cutting or tearing of the anterior rim. A beer can or can opener capsulorhexis, on the other hand, produces an anterior capsular rim which is not intact and has an inner scalloped edge having stress-inducing regions that render the rim very prone to tearing during surgery or subsequent fibrosis. An envelope capsulorhexis inherently produces an anterior capsular remnant which is ruptured and not intact.

A ruptured anterior capsular remnant or rim may preclude utilization of a simple plate haptic lens of the invention for the following reasons. A ruptured rim may not firmly retain the lens haptics in the sulcus of the capsular bag during fibrosis, thereby rendering the lens prone to decentration and/or posterior or anterior dislocation. A ruptured capsular rim may be incapable of assuming the taut trampoline-like condition of a non-ruptured rim. If so, a ruptured capsular rim is incapable of effecting full posterior deflection of a plate haptic lens to a distant viewing position against the posterior capsule during and after fibrosis. In fact, a ruptured capsular rim may permit anterior deflection of the lens. In either case, since the power of the lens is selected for each individual patient and is dependent upon their spectacle power, and since good vision without glasses requires the lens optic to be at precisely the correct distance from the retina, a simple plate haptic lens of the invention may not be acceptable for use with a ruptured anterior capsular remnant or rim.

The accommodating plate haptic spring lenses of the invention are designed for use when the anterior capsular remnant or rim of the capsular bag is ruptured. These plate haptic spring lenses are similar to the simple plate haptic lenses but have resilient springs, such as spring loops, at the ends of the plate haptics. When a plate haptic spring lens is implanted in a capsular bag, the haptic springs press outward against the wall of the capsular bag sulcus to fixate the lens in the bag during fibrosis. Fibrosis occurs about the springs in such a way as to effect fusion of the ruptured anterior remnant to the posterior capsule, firm fixation of the springs and hence the haptics in the bag, and posterior deflection of the lenses against the elastic posterior capsule during fibrosis. Brain-induced constriction and relaxation of the ciliary muscle after fibrosis with a ruptured capsular rim effects accommodation of the plate haptic spring lens in much the same way as occurs with the simple plate haptic lens and an intact non-ruptured capsular rim.

While the plate haptic; spring lenses of the invention are designed for use with a ruptured anterior capsular remnant or rim, these lenses can also be utilized with an intact rim. A plate haptic spring lens also compensates for improper lens placement in the eye with one end of the lens situated in the capsular bag and the other end of the lens situated in the ciliary sulcus of the eye. In this regard, an advantage of the plate haptic spring lenses of the invention over the simple plate haptic lenses resides in the fact that the spring lenses eliminate the need to have on hand in the operating room both a simple plate haptic lens for use with an intact capsular rim and a plate haptic spring lens as a substitute for the plate haptic lens in the event the rim is ruptured during surgery.

Another advantage of the plate haptic spring lenses over the simple plate haptic lenses of the invention resides in the fact that-the haptic spring lenses permit an optic of larger diameter than those of simple plate haptic lenses whose optic diameters will normally be restricted to the range of 4–7 mm. Thus, the haptic spring lenses rely on the haptic springs rather than the capsular remnant or rim to retain the lenses in position during fibrosis. As a consequence, these lenses may be used with a capsular remnant or rim of reduced radial width or a capsular rim which is slit or torn, both of which rim types provide a capsulotomy of larger effective size than those possible with a simple plate haptic lens. A larger capsulotomy, in turn, permits a larger optic diameter which offers certain opthalmological benefits. According to one aspect of this invention, such a large capsulotomy is provided after fibrosis is complete by using a laser to slit the anterior capsular rim radially or cut the rim circumferentially to enlarge the capsulotomy.

A further aspect of the invention concerns a novel method of utilizing an accommodating lens of the invention to provide accommodation in a human eye whose natural lens matrix has been removed from the lens capsule by a procedure involving capsulorhexis of the anterior capsule of the natural lens. The method may be utilized to replace a natural lens from which a cataract has been removed and to correct a refractive error in the eye of a patient who previously wore glasses in order to enable the patient to see well without glasses. For example, the invention can be utilized to correct refractive errors and restore accommodation persons in their mid-40's who require reading glasses or bifocals for near vision by replacing the clear non-cataractous crystalline lens matrix of their eyes with an accommodating intraocular lens according to the invention. According to the method of utilizing a plate haptic spring lens of the invention, the anterior capsular remnant or rim of the capsular bag is slit radially or cut to enlarge the anterior capsulotomy after capsulorhexis is complete to permit the use of a lens with a relatively large diameter optic larger than 6 or 7 min.

BRIEF DESCRIPTION OF THE DRAWINGS

FIG. 1 is a section through a human eye from which the natural lens matrix has been removed by a surgical procedure involving capsulorhexis of the natural lens, and illustrating an accommodating simple plate haptic accommodating lens according to this invention implanted within the capsular bag of the eye;

FIG. 1A is a section through a normal human eye;

FIG. 2 is an anterior side view of the intraocular lens of FIG. 1;

FIG. 3 is a section taken on line 3—3 in FIG. 2;

FIG. 4 is a section taken on line 4—4 in FIG. 1;

FIGS. 5—8 illustrate the manner in which the intraocular lens of FIGS. 1–4 is utilized in the eye of FIG. 1 to provide accommodation;

FIGS. 25–30 are anterior side views of modified accommodating intraocular lenses according to the invention having separate fixation means for fixing the lenses in the capsular bag of a human eye like that in FIG. 1;

DESCRIPTION OF THE PREFERRED EMBODIMENTS

Figure 9:
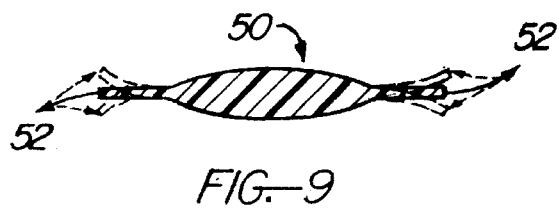
FIGS. 9–12 are sections, similar to FIG. 3, through modified accommodating intraocular lenses according to the invention having alternative optical shapes.
Figure 10:
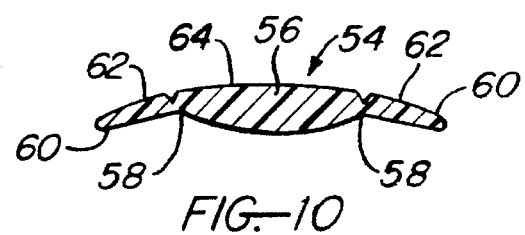

Turning now to these drawings and first to FIGS. 1 and 1A, there is illustrated a human eye 10 from which the natural crystalline lens matrix was previously removed by a surgical procedure involving continuous tear circular capsulorhexis of the natural lens L of the eye. The natural lens comprises a lens capsule having elastic anterior and posterior walls A and P, respectively, which are referred to by ophthalmologists and herein as anterior and posterior capsules, respectively. Within the lens capsule is a normally optically clear crystalline lens matrix M. In many individuals, this lens matrix becomes cloudy with advancing age and forms what is called a cataract. It is now common practice to restore a cataract patient's vision by removing the cataract from the natural lens and replacing the lens matrix by an artificial intraocular lens.

As mentioned earlier, continuous tear circular capsulorhexis involves tearing the anterior capsule A along a generally circular tear line in such a way as to form a relatively smooth-edged circular opening or capsulotomy in the center of the anterior capsule. The cataract is removed from the natural lens capsule through this capsulotomy. After completion of this surgical procedure, the eye includes an optically clear anterior cornea 12, an opaque sclera 14 on the inner side of which is the retina 16 of the eye, an iris 18, a capsular bag 20 behind the iris, and a vitreous cavity 21 behind the capsular bag filled with the gel-like vitreous humor. The capsular bag 20 is the structure of the natural lens of the eye which remains intact within the eye after the continuous tear circular tear capsulorhexis has been performed and the natural lens matrix has been removed from the natural lens.

The capsular bag 20 includes an annular anterior capsular remnant or rim 22 and an elastic posterior capsule 24 which are joined along the perimeter of the bag to form an annular crevice-like capsular bag sulcus 25 between rim and posterior capsule. The capsular rim 22 is the remnant of the anterior capsule of the natural lens which remains after capsulorhexis has been performed on the natural lens. This rim circumferentially surrounds a central, generally round anterior opening 26 (capsulotomy) in the capsular bag through which the natural lens matrix was previously removed from the natural lens. The capsular bag 20 is secured about its perimeter to the ciliary muscle of the eye by zonules 30.

Natural accommodation in a normal human eye having a normal human crystalline lens involves automatic contraction or constriction and relaxation of the ciliary muscle of the eye by the brain in response to looking at objects at different distances. Ciliary muscle relaxation, which is the normal state of the muscle, shapes the human crystalline lens for distant vision. Ciliary muscle contraction shapes the human crystalline lens for near vision. The brain-induced change from distant vision to near vision is referred to as accommodation.

Implanted within the capsular bag 20 of the eye 10 is an accommodating intraocular lens 32 according to this invention which replaces and performs the accommodation function of the removed human crystalline lens. Lens 32 is referred to in places as a simple plate haptic lens to distinguish it from the later described plate haptic spring lens of the invention, As mentioned earlier and will become readily understood as the description proceeds, the accommodating intraocular lens may be utilized to replace either a natural lens which is virtually totally defective, such as a cataractous natural lens, or a natural lens that provides satisfactory vision at one distance without the wearing of glasses but provides satisfactory vision at another distance only when glasses are worn. For example, the accommodating intraocular lens of the invention can be utilized to correct refractive errors and restore accommodation for persons in their mid-40's who require reading glasses or bifocals for near vision.

Intraocular lens 32 comprises a body 33 which may be formed of relatively hard material, relatively soft flexible semi-rigid material, or a combination of both hard and soft materials. Examples of relatively hard materials which are suitable for the lens body are methyl methacrylate, polysulfones, and other relatively hard biologically inert optical materials. Examples of suitable relatively soft materials for the lens body are silicone, hydrogels, thermolabile materials, and other flexible semi-rigid biologically inert optical materials.

The lens body 33 has a generally rectangular shape and includes a central optical zone or optic 34 and plate haptics 36 extending from diametrically opposite edges of the optic. The haptics have inner ends joined to the optic and opposite outer free ends. The haptics 36 are movable anteriorly and posteriorly relative to the optic 34, that is to say the outer ends of the haptics are movable anteriorly and posteriorly relative to the optic. The particular lens embodiment illustrated is constructed of a resilient semi-rigid material and has flexible hinges 38 which join the inner ends of the haptics to the optic. The haptics are relatively rigid and are flexible about the hinges anteriorly and posteriorly relative to the optic. These hinges are formed by grooves 40 which enter the anterior side of the lens body and extend along the inner ends of the haptics. The haptics 36 are flexible about the hinges 38 in the anterior and posterior directions of the optic. The lens has a relatively flat unstressed configuration, illustrated in FIGS. 2 and 3, wherein the haptics 36 and their hinges 38 are disposed in a common plane transverse to the optic axis of the optic 34. Deformation of the lens from this unstressed configuration by anterior or posterior deflection of the haptics about their hinges 38 creates in the hinges elastic strain energy forces which bias the lens to its unstressed configuration. If the lens is constructed of a relatively hard optic material, it may be necessary to replace the flexible hinges 38 by pivotal hinges of some kind. In a later described lens embodiment of the invention, the haptic hinges are eliminated, and the haptics are made flexible throughout their length.

The accommodating intraocular lens 32 is implanted within the capsular bag 20 of the eye 10 in the position shown in FIGS. 1 and 5. When implanting the lens in the bag, the ciliary muscle 28 of the eye is maintained in a relaxed state in which the muscle stretches the capsular bag 20 to its maximum diameter. The lens is inserted into the bag through the anterior capsular capsulotomy 26 and placed in the position shown in FIGS. 1 and 4. In this position, the lens optic 34 is aligned on the axis of the eye with the capsolotomy, the posterior side of the lens faces the elastic posterior capsule 24 of the bag, and the outer ends of the lens haptics 36 are situated within the sulcus 25 at the radially outer perimeter of the bag. The overall length of the lens substantially equals the inner diameter (10–11 mm) of the stretched capsular bag so that the lens fits snugly within the stretched capsular bag, as shown. This prevents decentration of the lens and thereby permits the optic 34 to be smaller such that it can move forward inside the capsular rim during the later described accommodation.

During a post-operative healing period on the order of two to three weeks following surgical implantation of the lens 32 in the capsular bag 20, epithelial cells under the anterior capsular rim 22 of the bag cause fusion of the rim to the posterior capsule 24 by fibrosis. This fibrosis occurs around the lens haptics 36 in such a way that the haptics are "shrink-wrapped" by the capsular bag 20, and the haptics form pockets 42 in the fibrosedmaterial F (FIGS. 4 and 6–8). These pockets position and center the lens in the eye. In order to insure proper formation of the haptic pockets 42, sufficient time must be allowed for fibrosis to occur to completion without flexing of the lens haptics 36 by ciliary muscle action. One way of accomplishing this is to have the patient periodically administer cycloplegic drops, such as Atropine, into his eye during the post-operative fibrosis period. These drops maintain the ciliary muscle 28 in its relaxed state. In this relaxed state, the capsular bag 20 is stretched to its maximum diameter, and the anterior capsular rim 22 is stretched to a taut trampoline-like condition or position. The rim fibroses from this taut condition.

The capsular rim 22 shrinks during fibrosis and thereby shrinks the capsular bag 20 slightly in its radial direction. This shrinkage combined with shrink wrapping of the lens haptics 36 produces opposing endwise compression forces on the ends of the haptics which tend to buckle or flex the lens at its hinges 38 and thereby move the lens optic 34 along the axis of the eye. Unless restrained, this flexing of the lens might occur either forwardly or rearwardly. The taut anterior capsular rim 22 pushes rearwardly against and thereby prevents forward flexing of the lens. Accordingly, endwise compression of the lens during fibrosis aided by the rearward thrust of the taut capsular rim against the lens haptics 36 causes rearward flexing of the lens from its initial position of FIGS. 1 and 5 to its position of FIG. 6. The lens haptics 36 are made sufficiently rigid that they will not be bent or bowed by the forces of fibrosis. At the conclusion of fibrosis, the lens occupies its posterior position of FIG. 6 wherein the lens presses rearwardly against the elastic posterior capsule 24 and stretches this capsule rearwardly. The posterior capsule then exerts a forward elastic bias force on the lens. This posterior position of the lens is its distant vision position.

Another way of preventing ciliary muscle induced flexing of the lens 32 during fibrosis is to place sutures within the hinge grooves 40. Removal of these sutures after completion of fibrosis may be accomplished by using sutures that are either absorbable in the fluid within the eye or by using sutures made of a material, such as nylon, which can be removed by a laser.

Natural accommodation in a normal human eye involves shaping of the natural crystal line lens by automatic contraction and relaxation of the ciliary muscle of the eye by the brain to focus the eye at different distances. Ciliary muscle relaxation shapes the natural lens for distant vision. Ciliary muscle contraction shapes the natural lens for near vision.

The accommodating intraocular lens 32 is uniquely constructed to utilize this same ciliary muscle action, the fibrosed capsular rim 22, the elastic posterior capsule 24, and the vitreous pressure within the vitreous cavity 21 to effect accommodation movement of the lens optic 34 along the optic axis of the eye between its distant vision position of FIG. 6 to its near vision position of FIG. 8. Thus, when looking at a distant scene, the brain relaxes the ciliary muscles 28. Relaxation of the ciliary muscle stretches the capsular bag 20 to its maximum diameter and its fibrosed anterior rim 22 to the taut trampoline-like condition or position discussed above. The taut rim deflects the lens rearwardly-to its posterior distant vision position of FIG. 6 in which the elastic posterior capsule 24 is stretched rearwardly by the lens and thereby exerts a forward bias force on the lens. When looking at a near scene, such as a book when reading, the brain constricts or contracts the ciliary muscle. This ciliary muscle contraction has the three-fold effect of increasing the vitreous cavity pressure, relaxing the capsular bag 20 and particularly its fibrosed capsular rim 22, and exerting opposing endwise compression forces on the ends of the lens haptics 36 with resultant endwise compression of the lens. Relaxation of the capsular rim permits the rim to flex forwardly and thereby enables the combined forward bias force exerted on the lens by the rearwardly stretched posterior capsule and the increased vitreous cavity pressure to push the lens forwardly in an initial accommodation movement from the position of FIG. 6 to the intermediate accommodation position of FIG. 7.

In this intermediate accommodation position, the lens is substantially flat, and the ends of the lens haptics and their hinges 38 are disposed substantially in a common plane normal to the axis of the eye. During the initial accommodation, the lens arches rearwardly so that endwise compression of the lens by ciliary muscle contraction produces a rearward buckling force on the lens which resists the initial accommodation. However, the increased vitreous cavity pressure and the forward bias force of the stretched posterior capsule are sufficient to overcome this opposing rearward buckling force and effect forward accommodation movement of the lens to and at least just slightly beyond the intermediate position of FIG. 7. At this point, endwise compression of the lens by the contracted ciliary muscle produces a forward buckling force on the lens which effects final accommodation of the lens beyond the intermediate position of FIG. 7 to the near vision position of FIG. 8. Subsequent brain-induced relaxation of the ciliary muscle 28 in response to looking at a distant scene reduces the vitreous cavity pressure, stretches the capsular bag 20 to its maximum diameter, and restores the anterior capsular rim 22 to its taut trampoline-like condition to effect return of the lens to its distant viewing position of FIG. 6. During accommodation, the lens optic 34 moves along the axis of the eye toward and away from the retina 16. The power of the optic is selected by the brain to sharply focus incoming light rays on the retina throughout the range of this accommodation movement.

The lens haptics 36 flex at their hinges 38 with respect to the lens optic 34 during accommodation. Any elastic strain energy forces developed in the hinges during this flexing produces additional anterior and/or posterior forces on the lens. For example, assume that the lens is relatively flat, i.e. if the lens haptics 36 lie in a common plane as shown in FIG. 1, in the normal unstressed state of the lens. In this case, posterior deflection of the lens from its position of FIG. 1-to its distant vision position of FIG. 6 creates elastic strain energy forces in the hinges 38 which urge the lens forwardly back to its unstressed position of FIGS. 1 and thus aid the above discussed initial accommodation of the lens in response to contraction of the ciliary muscle. Final accommodation flexing of the lens from its intermediate position of FIG. 7 to its near vision position of FIG. 8 creates elastic strain energy forces in the hinges 38 which urge the lens rearwardly toward its unstressed position and thus aid initial return of the lens from its near vision position to its distant vision position in response to relaxation of the ciliary muscle. The lens may be designed to assume some other normal unstressed position, of course, in which case any elastic strain energy forces created in the lens during flexing of the haptics will aid, resist, or both aid and resist accommodation of the lens to its near vision position and return of the lens to its distant vision position depending upon the unstressed position of the lens.

During accommodation, the lens haptics 36 slide endwise in their fibrosed tissue pockets 42. As shown best in FIGS. 2 and 3, the haptics are tapered endwise in width and thickness to enable the haptics to move freely in the pockets. The lens optic 34 moves toward and away from the anterior capsular rim 22. The diameter of the optic is made as large as possible to maximize its optical imaging efficiency. The optic is preferably but not necessarily made smaller than the diameter of the capsulotomy 26 to permit accommodation movement of the optic into and from the capsulotomy without interference by the capsular rim 22 in order to maximize the accommodation range. The actual lens dimensions are determined by each patient's ocular dimensions. The dimensions of a simple plate haptic intraocular lens according to the invention will generally fall within the following ranges:

Optic diameter: 3.0 mm–7.0 mm

Overall lens length: 9.0 mm–11.5 mm

Haptic thickness: 0.25 mm–0.35 mm

Figure 11:
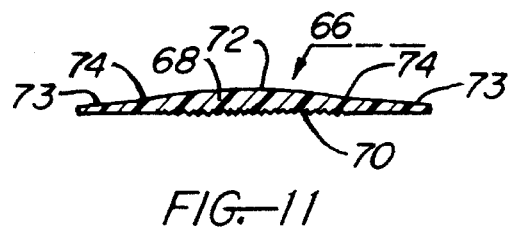
Figure 12:
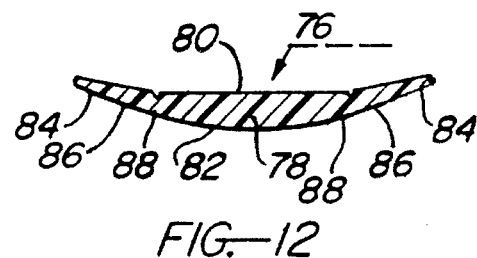
Figure 13:
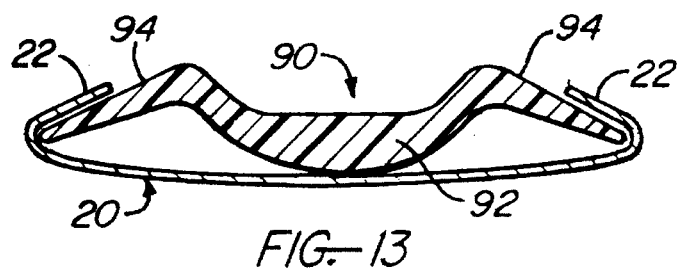
FIG. 13 is a section similar to FIG. 3 through a modified accommodating intraocular lens according to the invention illustrating the lens in its normal unstressed configuration.
Figure 14:
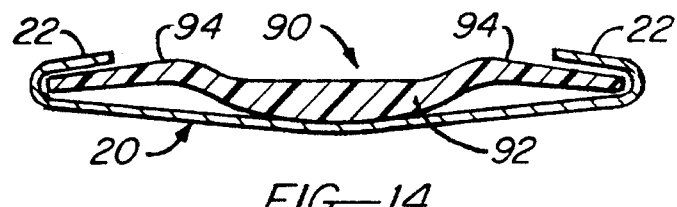
FIG. 14 is a section similar to FIG. 16, illustrating the lens in its distant vision position.
Figure 15:
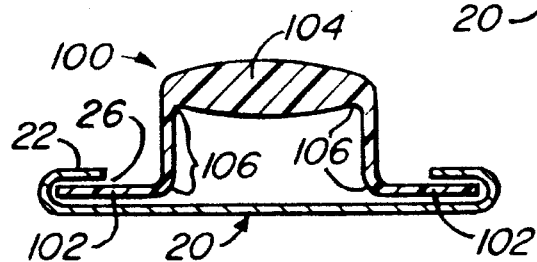
FIG. 15 is a section through a modified accommodating intraocular lens according to he invention having an anteriorly displaced optic.

Refer now to FIGS. 9–15 illustrating several possible alternative shapes of the accommodating intraocular lens. The modified lens 50 illustrated in FIG. 9 is identical to lens 32 of FIGS. 1–8 except that the haptic hinges 38 of lens 32 are eliminated in the lens 50, and the haptics 52 of the lens 50 are flexible throughout their length, as illustrated by the broken lines in FIG. 9. The modified lens 54 in FIG. 10 has an anteriorly arched unstressed shape and includes a biconvex optic 56, flexible hinges 58, and anteriorly vaulted haptics 60 with convex anterior surfaces 62. The convex anterior face 64 of the optic 56 and the convex anterior haptic surfaces 62 are rounded to a common radius. The modified intraocular lens 66 in FIG. 11 is relatively flat and includes an optic 68 having a planar Fresnel anterior face 70 and a convex posterior face 72, haptics 73, and flexible haptic hinges 74. The modified lens 76 in FIG. 12 has a posteriorly arched unstressed shape and includes an optic 78 having a planar anterior face 80 and a convex posterior face 82, haptics 84 having convex posterior surfaces 86 and haptic hinges 88. The posterior face 82 of the optic 78 and the posterior surfaces 86 of the haptics 84 are rounded to a common radius. The modified lens 90 illustrated in FIGS. 13 and 14 includes an optic 92 and flexible haptics 94 and has an unstressed near vision configuration shown in FIG. 13. The haptics flex to permit posterior deflection of the lens to its distant vision configuration of FIG. 14. The optic 92 is posteriorly offset relative to the inner ends of the haptics to permit greater anterior displacement of the optic during accommodation without contacting the anterior capsular rim 22 of the capsular bag 20. The modified intraocular lens 100 of FIG. 15 includes haptics 102 and an optic 104 which is offset anteriorly relative to the inner ends of the haptics. The haptics are joined to diametrically opposite sides of the optic by flexible hinges 106.

The modified intraocular lenses of FIGS. 9–15 are implanted within the capsular bag 20 of the eye 10 and utilize the posterior bias of the fibrosed capsular rim 22, the posterior capsule 24, changes in vitreous cavity pressure, and the patient's ciliary muscle action to effect accommodation in the same manner as described in connection with the intraocular lens 32 of FIGS. 1–8. In the case of the lens 100 in FIG. 15, the outer ends of its haptics 102 are implanted within the capsular bag 20 in essentially the same way as the haptics of lens 32 so that fibrosis of the rim 22 occurs about the haptics in the same manner as described in connection with FIGS. 1–8. The anteriorly offset optic 104 of the lens 100, on the other hand, protrudes through the anterior opening 26 in the capsular bag 20 and is situated anteriorly of the rim and between the rim and the iris 18 of the eye. There is sufficient space between the rim and the iris to accommodate the optic of a properly sized lens without the optic contacting the iris.

Figure 16:
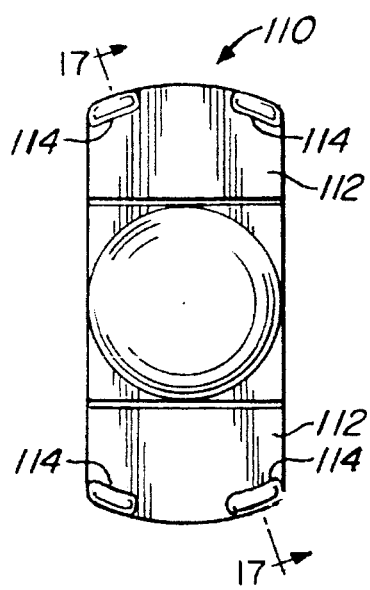
FIG. 16 is an anterior side view of a modified accommodating intraocular lens according to the invention having integral fixation means for fixing the lens in the capsular bag of the eye.
Figure 17:
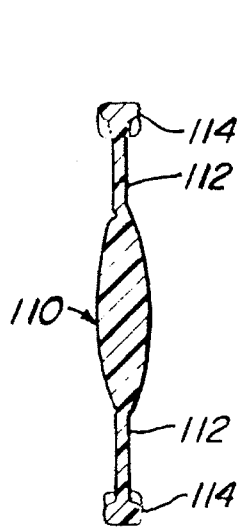
FIG. 17 is a section taken on line 17—17 in FIG. 16.
Figure 18:
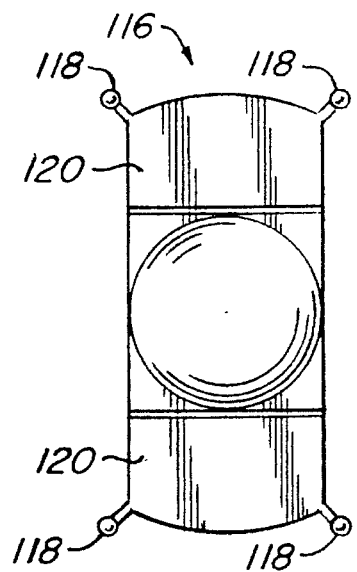
FIG. 18–21 are anterior side views of modified accommodating intraocular lenses according to the invention having alternative integral fixation means for fixing the lenses in the capsular bag of the eye.
Figure 19:
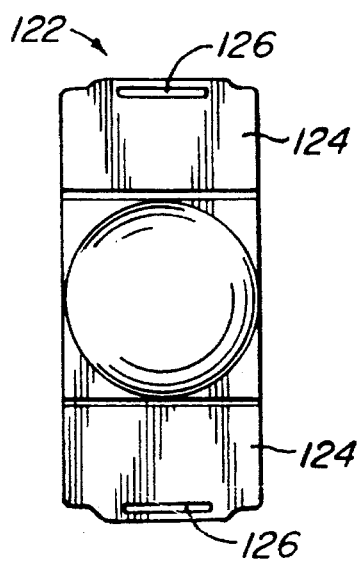
Figure 20:
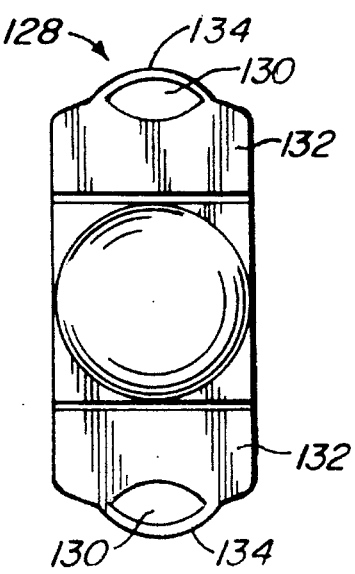

FIGS. 16–20 illustrate modified accommodating intraocular lenses according to the invention having means for fixating or anchoring the lens haptics in the capsular bag 20 to prevent the lenses from entering the vitreous cavity 21 of the eye in the event that the posterior capsule 24 becomes torn or a posterior capsulotomy must be performed on the posterior capsule because it becomes hazy. Except as noted below, the modified intraocular lenses of FIGS. 16–20 are identical to the lens 32 of FIGS. 1–8 and are implanted in the capsular bag 20 of the eye 10 in the same manner as described in connection with FIGS. 1–8. The intraocular lens 110 of FIGS. 16 and 17 is identical to lens 32 except that the outer ends of the lens haptics 112 have raised shoulders 114. Fibrosis of the capsular rim 22 around the haptics 112 and their shoulders 114 anchors or fixates the lens 110 in the capsular bag 20. The intraocular lens 116 of FIG. 18 is identical to lens 32 except that flexible stalk-like knobs 118 extend diagonally from the outer ends of the lens plate haptics 120. The distance between the outer ends of the diametrically opposed knobs 118 is slightly larger than the distance between the outer ends of the lens haptics and slightly larger than the diameter of the capsular bag 20. The knobs are set wider than the width of the lens body. These two features help to center the intraocular lens within the capsular bag so that the lens optic is centered immediately behind the circular capsulotomy 26 in the bag. Fibrosis of the capsular rim 22 around the haptics 120 and their knobs 118 fixes the lens 116 in the capsular bag 20. The intraocular lens 122 of FIG. 19 is identical to lens 32 except that the outer ends of the lens haptics 124 have openings 126. Fibrosis of the capsular rim 22 occurs around the haptics 124 and through their openings 126 to fixate the lens 122 in the capsular bag 20. The intraocular lens 128 of FIG. 20 is similar to the lens 122 in that the lens 128 has openings 130 in the outer ends of its haptics 132 through which fibrosis of the capsular rim 22 occurs to fixate the lens in the capsular bag 20. Unlike the lens 122, however, the haptic openings 130 are bounded along the outer ends of the haptics by spring loops 134. The overall length of the lens 128, measured between the centers of the spring loops 134 is made slightly greater than the maximum diameter of the capsular bag. The spring loops 134 press against and are deformed inwardly slightly by the outer circumference of the capsular bag to center the lens in the eye during fibrosis.

Figure 21:
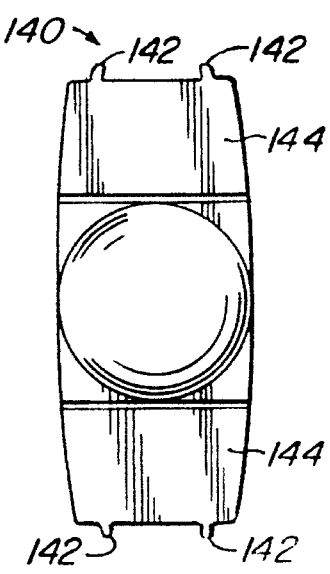

The modified intraocular lens 140 of FIG. 21 is identical to the lens 32 of FIGS. 1–8 except that the lens 140 has centration nipples 142 projecting endwise from the outer ends of the lens haptics 144 to compensate for slight differences, from one patient to another, in the diameter of the human capsular bag 20. Thus, the diameter of the capsular bag varies from about 11 mm in high myopes to about 9.5 mm in high hyperopes. The centration nipples 142 prevent differences in the degree of flexing of the haptics 144 in capsular bags of different diameters. For example, in a hyperopic eye with a small capsular bag, the lens haptics would flex more with marked posterior vaulting of the lens by the fibrosed capsular rim compared to the minimal vaulting of the haptics which would occur in high myopes with relatively large capsular bags. The nipples indent themselves into the outer circumference of the capsular bag to compensate for such differing bag diameters and thereby center the lens in the bag.

Figure 22:
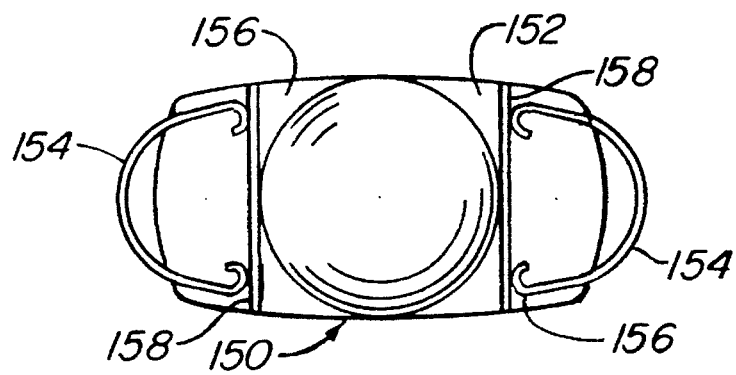
FIG. 22 is an anterior side view of a modified accommodating intraocular lens according to the invention having springs for aiding accommodation.
Figure 23:
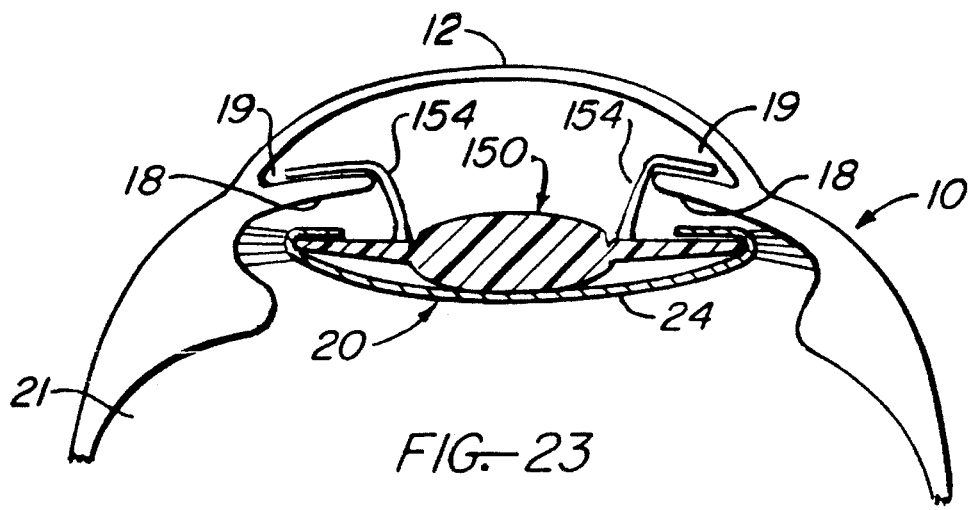
FIG. 23 illustrates the lens of FIG. 22 implanted within the capsular bag of a human eye like that in FIG. 1, and showing the lens in the position which the lens occupies immediately after surgery as well as after a certain degree of accommodation.
Figure 24:
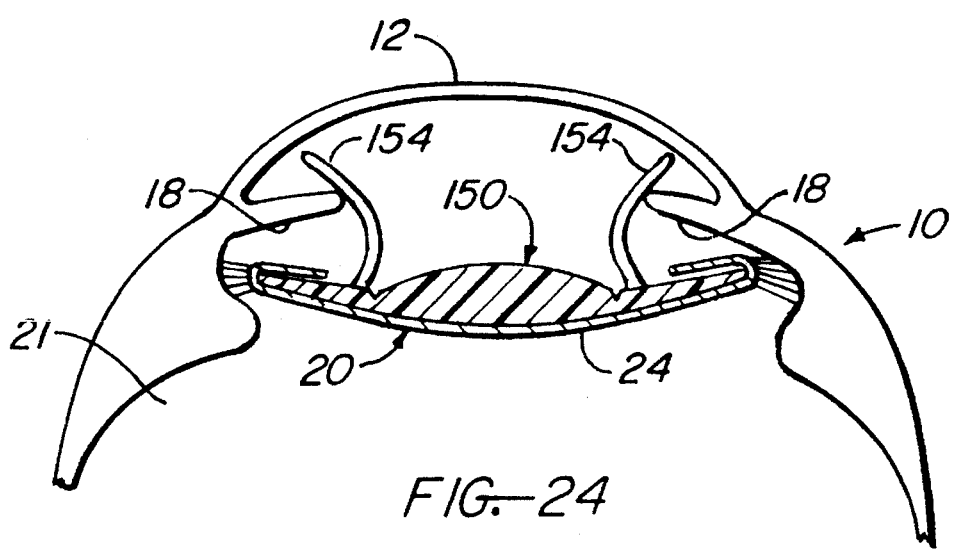
FIG. 24 is a view similar to FIG. 23 showing the lens in its posterior distant vision position.

The modified intraocular lens 150 illustrated in FIGS. 22–24 comprises a lens body 152 proper identical to that of FIGS. 1–8 and springs 154 in the form of U-shaped hoops constructed of biologically inert spring material. The ends of these springs are fixed to the anterior sides of the lens haptics 156 adjacent the haptic hinges 158 in such a way that the arched ends of the springs extend a small distance beyond the outer ends of the haptics. The springs are stressed to normally lie relatively close to the anterior sides of the haptics. The lens body 152 is implanted within the capsular bag 20 of the eye 10 in the same way as described in connection with the lens 32 of FIGS. 1–8, and with the outer arched ends of the lens springs 154 lodged within the sulcus 19 of the eye between the iris 18 and the cornea 12. When the lens is in the position of FIG. 23 which it occupies immediately after surgery as well as after some degree of accommodation, the springs 154 lie relatively close to the anterior sides of the lens haptics 156. During posterior displacement of the lens to its distant vision position of FIG. 24 by the posterior bias of the fibrosed capsular rim 22, the springs are deflected anteriorly away from the lens haptics, as shown, thereby creating in the springs elastic strain energy forces which aid the stretched posterior capsule 24 and vitreous cavity pressure in displacing the lens anteriorly during accommodation in response to contraction of the ciliary muscle 28.

FIGS. 25–32 illustrate modified intraocular lenses according to the invention having a lens body and separate lens fixation elements for positioning the lenses in the capsular bag 20. Fibrosis of the capsular rim 22 occurs around these fixation elements in a manner which securely fixes the elements within the bag. In some figures, the lens body is separable from the fixation elements to permit removal of the lens from and replacement of the lens in its original position in the eye. In other figures, the lens body and fixation elements are secured against separation to prevent entrance of the lens body into the vitreous chamber in the event a tear develops in the posterior capsule 24 of the bag or a posterior capsulotomy is performed in the capsule.

Figure 25:
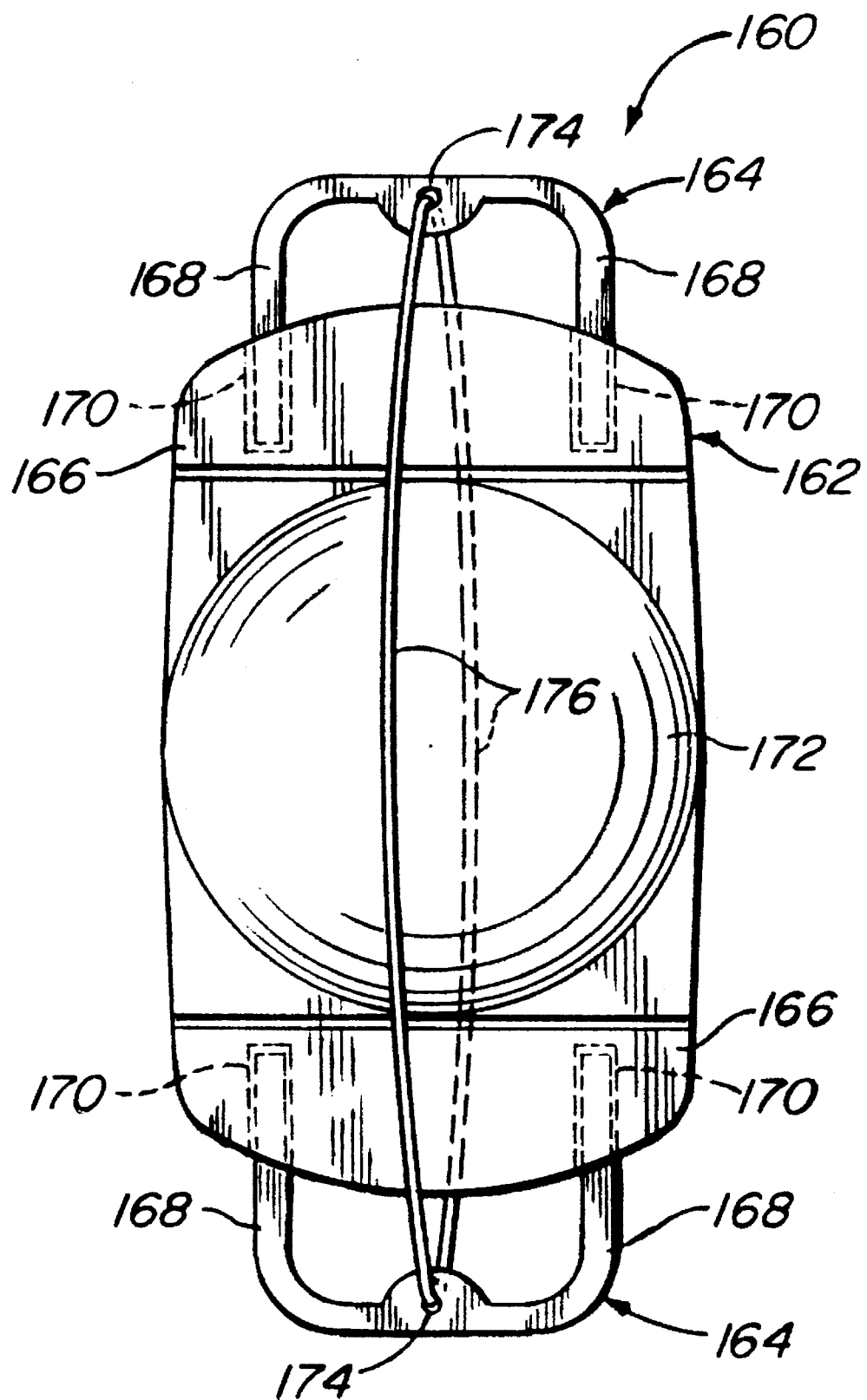

The modified lens 160 of FIG. 25 includes a lens body 162 which is identical, except as noted below, to that of lens 32 in FIGS. 1–8 and separate fixation elements 164 at the outer ends of the lens haptics 166. The fixation elements and haptics are interengaged in such a way that the elements and haptics are capable of relative movement lengthwise of the haptics when the haptics flex during accommodation of the lens. The fixation elements 164 in FIG. 25 are generally U-shaped loops of biologically inert material having legs 168 which slide within longitudinal sockets 170 entering the outer ends of the haptics 166. The haptics 166 are somewhat shorter in length than those of the lens 32, and the overall length of the lens, measured between the outer arched ends of the fixation loops 164, when their legs 168 abut the bottoms of their sockets 170, is less than the maximum diameter of the capsular bag 20 when the ciliary muscle 28 is relaxed and greater than the diameter of the bag when the ciliary muscle is fully contracted for accommodation. The lens 160 is implanted within the capsular bag 20 of the eye 10 with the fixation loops 164 and the outer ends of the haptics 166 disposed between the anterior rim 22 and posterior capsule 24 of the capsular bag 20. The outer arched ends of the loops are situated at the outer circumference of the bag.

Fibrosis of the capsular rim 22 occurs around the outer ends of the lens haptics 166 and the exposed outer ends of the fixation loops 164 and through the spaces between the haptics and the loops in such a way that the loops are firmly fixed in the capsular bag, and the haptics form pockets 42 in the fibrose tissue F. The posterior bias of the fibrosed capsular rim. 22 urges the lens posteriorly to its distant vision position when the ciliary muscle 28 is relaxed, thereby stretching the posterior capsule 24 rearwardly in the same manner as explained in connection with FIGS. 1–8. When the ciliary muscle contracts during accommodation, the vitreous cavity pressure increases and the capsular rim 22 relaxes, thereby permitting the stretched posterior capsule and the vitreous cavity pressure to push the lens body 162 forwardly toward its near vision position, again in the same manner as explained in connection with FIGS. 1–8. Contraction of the capsular bag in response to contraction of the ciliary muscle during accommodation displacement exerts inward forces on the fixation loops 164. These inward forces urge the loops inwardly in their haptic sockets 170 until the loops abut the bottoms of the sockets. The inward forces exerted on the loops then produce an anterior buckling moment on the lens body 162 which aids accommodation of the lens by the posterior capsule. During this accommodation, the lens haptics 166 flex posteriorly relative to the lens optic 172 and slide inwardly in their fibrose pockets 42 and along the legs 168 of the fixation loops 164, the movement being aided by hinges 38.

The fixation loops have holes 174 in their outer arched ends through which a suture 176 may be passed and tied to retain the loops and lens body in assembled relation during implantation of the lens in the capsular bag. This suture is removed at the conclusion of the surgery. Holes 174 may also be utilized to position the lens in the capsular bag during surgery. The lens haptics 166 are separable from and reengageable with the fixation loops 164. This permits the lens body 162 to be removed from the eye any time after surgery for correction or replacement of the lens optic 172 and then replaced in its original position in the eye.

Figure 26:
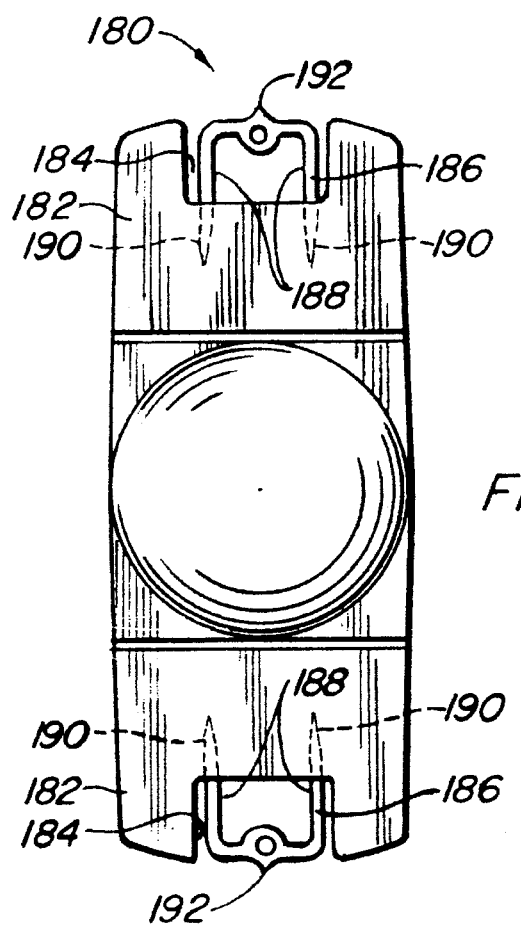

The modified intraocular lens 180 of FIG. 26 is similar to that of FIG. 25 except for the following differences. First, the haptics 182 of lens 180 are substantially the same length as the haptics of lens 32 and have cutouts 184 in their outer ends. The legs 188 of the fixation loops 186 slide in sockets 190 which enter the bottom edges of the cutouts 184. When the lens is implanted within the capsular bag 20, the tongue-like haptic portions at opposite sides of the haptic cutouts 184 and the outer arched ends of the fixation loops 186 are situated within the outer circumference of the bag. As with the lens of FIG. 25, fibrosis of the capsular rim 22 occurs around the haptics 182 and fixation loops 186 and through the spaces between the haptics and loops so as to firmly fix the loops in the capsular bag and form pockets within which the haptics slide when they flex during accommodation of the lens. Secondly, the legs 188 of the fixation loops 186 and their sockets 190 in the lens haptics 182 are tapered to facilitate free relative movement of the loops and haptics when the haptics flex during accommodation. Thirdly, the fixation loops have fixation nipples 192 at their outer arched ends which indent into the outer circumference of the capsular bag 20 to retain the lens against movement relative to the bag during fibrosis.

Figure 27:
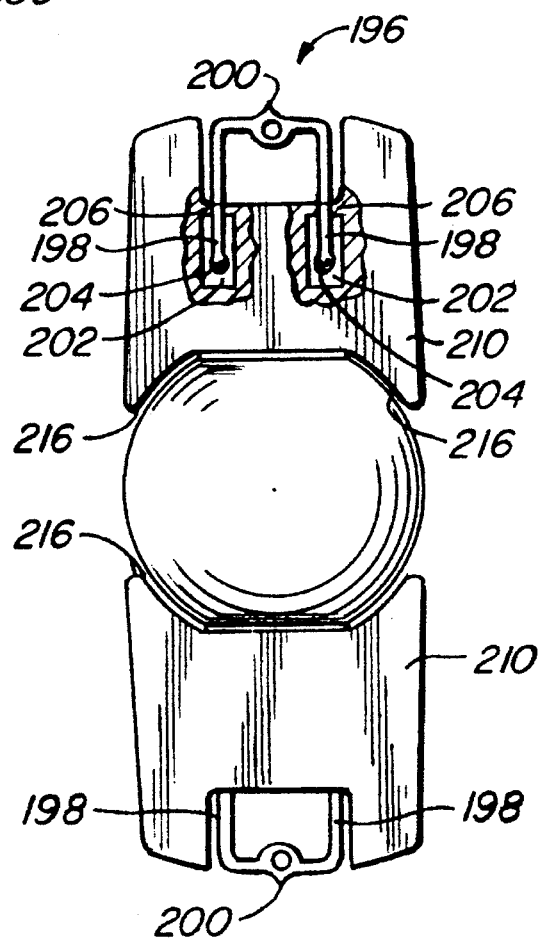

FIG. 27 illustrates a modified intraocular lens 196 like the lens 180 illustrated in FIG. 26 except that the legs 198 of the fixation loops 200 and the haptic sockets 202 which receive these legs have coacting shoulders 204, 206. These shoulders permit limited relative movement of the lens body 208 and loops when the haptics 210 flex during lens accommodation, but secure the lens body and loops against complete separation so as to prevent the lens body from entering the vitreous chamber 21 if a tear occurs or a capsulotomy is performed in the posterior capsule 24. Another difference between the lens 196 and the lens 180 resides in the fact that the hinges 212 connecting the inner ends of the haptics 210 to the lens optic 214 extend across only an intermediate portion of the haptic width. The remaining lateral portions of the inner haptic ends beyond the ends of the hinges are separated from the optic by arcuate slots 216 centered on the axis of the optic. These separations of the haptics from the optic permit the optic to move freely into and from the anterior opening or capsulotomy 26 in the capsular bag 20 without interference with the capsular rim 22 during lens accommodation. The generally triangular haptic portions adjacent the slots 216 prevent the rim 22 of the capsular bag 20 from fibrosing between the lens optic 214 and the inner ends of the lens haptics 210 and thereby restricting endwise movement of the haptics in their fibrosed pockets 42.

The modified lens 220 of FIG. 28 includes a lens body 222 and separate fixation elements 224 at the outer ends of the lens haptics 226. The inner ends of the haptics are convexly curved and disposed in generally tangential relation to diametrically opposite sides of the lens optic 228 so as to provide relatively large clearance spaces 230 between the optic and the inner haptic ends. The haptics and optic are joined along their tangential portions by flexible hinges 232. The fixation elements 224 are generally cruciform shaped pins having inner journals 234 which slide and rotate within bearing bores 236 entering the bottom edges of cutouts 238 in the outer ends of the haptics 226. These fixation pins have holes 240 between their ends, outer cross arms 242, and nipples 244 at their outer ends. The length of the lens 220 measured between the outer ends of its haptics 226 and fixation pins 224 approximates the maximum inner diameter of the capsular bag 20 when the ciliary muscle is relaxed. The fixation pin journals 234 and their bores 236 have coacting shoulders 246, 248 which permit limited relative movement of the lens body and fixation pins when the haptics flex during accommodation but secure the body and fixation pins against complete separation, for the same reasons as explained above in connection with FIG. 27. If desired, the shoulders 246, 248 may be eliminated to permit separation of the fixation pins and lens body for the same reasons as explained in connection with FIG. 26. If the shoulders are eliminated, a removable suture may be threaded through the fixation pin holes 240 and tied to hold the fixation pins and lens body in assembled relation during implantation of the lens, as explained in connection with FIG. 25. The holes may also be used to position the lens in the capsular bag during implantation of the lens.

When the lens 220 is implanted within the capsular bag 20 of the eye 10, the outer ends of the lens haptics 226 and the fixation pins 224 are disposed between the capsular rim 22 and posterior capsule 24 of the bag in much the same way as described in connection with FIGS. 25-27. The nipples 244 indent the outer circumference of the bag to fix the lens against rotation circumferentially around the bag and center the lens in the eye during fibrosis of the rim 22. Fibrosis of the capsular rim occurs about the outer ends of the haptics and the fixation pins to firmly fix the pins in the bag and form pockets in the fibrosed tissue receiving the haptics. The lens body 222 is urged posteriorly to its distant vision position by the posterior bias of the capsular rim 22 when the ciliary muscle 28 relaxes and anteriorly toward its near vision position during accommodation by the stretched posterior capsule 24 and increase in vitreous cavity pressure when the ciliary muscle contracts, all in essentially the same way as explained earlier in connection with FIGS. 25-27. During anterior accommodation of the lens, contraction of the capsular bag 20 in response to contraction of the ciliary muscle exerts inward forces on the outer ends of the haptics 226 which produce an anterior buckling moment on the lens body 222 that aids lens accommodation by the posterior capsule. The cross arms 242 of the fixation pins 224 are enveloped by the fibrosed tissue F during fibrosis of the rim 22 to provide pivots about which the pins can rotate during buckling of the lens body in the course of lens accommodation. The spaces 230 between the inner ends of the haptics 226 and the optic 228 accommodate movement of the optic into and from the opening 26 in the capsular bag without interference with the surrounding capsular rim 22.

The modified intraocular lenses 260, 262 in FIGS. 29 and 30 are identical to the lenses 180, 196, respectively, in FIGS. 26 and 27 except that the fixation loops of the latter lenses are replaced, in FIGS. 29 and 30, by fixation pins 264, 266 like those in FIG. 28.

Figure 31:
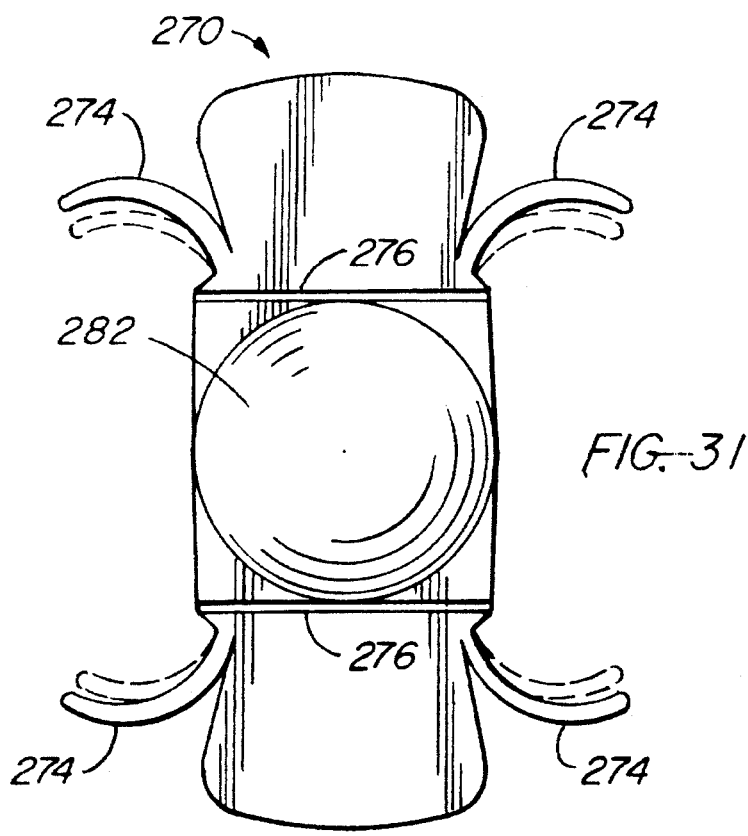
FIGS. 31–34 illustrate modified accommodating intraocular lenses according to the invention having integral fixation means.
Figure 32:
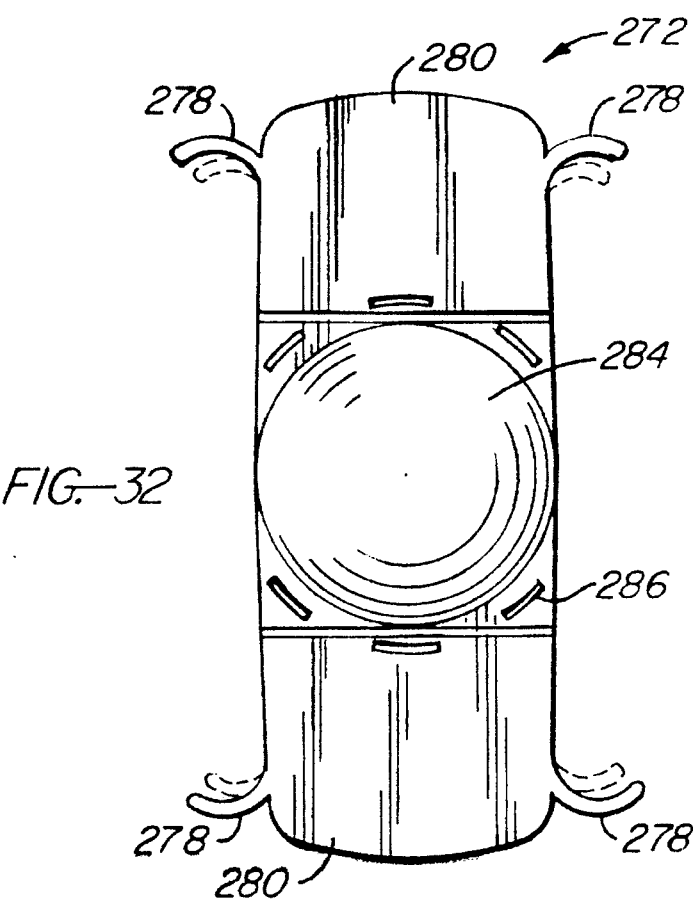

The modified intraocular lenses 270, 272 in FIGS. 31 and 32 are identical to the lens 32 of FIGS. 1-8 except that lens 270 has lateral spring arms 274 which extend from the haptic hinges 276 and lens 272 has lateral spring arms 278 which extend from the edges of the lens haptics 280. The arms 274, 278 extend laterally from and longitudinally toward the outer ends of the lens haptics in such a way that in their normal unstressed positions, the arms are disposed at acute angles relative to the longitudinal axes of the lenses. The arms are sized in length so that when the lenses are implanted within the capsular bag 20 of the eye, the outer ends of the arms press against the outer circumference of the bag and are thereby curled or compressed to the positions illustrated in broken lines. The curl or compression in the arms decreases when the capsular bag expands in response to relaxation of the ciliary muscle during distant vision accommodation of the lens and increases when bag contracts in response to contraction of the ciliary muscle during near vision accommodation of the lens. Engagement of the arms with the capsular bag circumference acts to center the lenses in the bag in a position wherein the lens optics 282, 284 are coaxially aligned with the anterior bag opening or capsulotomy. Fibrosis of the capsular rim 22 occurs about the spring arms to fix the lenses within the capsular bag and about the lens haptics to form pockets in which the haptics slide when they flex during accommodation of the lenses.

Referring to FIG. 32 and to FIGS. 4 to 8, projections such as those indicated at 286 in FIG. 32, may preferably be provided in various embodiments of the invention to space the capsulorhexis from the optic when the capsulorhexis constricts from its configuration shown in FIGS. 5 to 8. This spacing prevents the anterior capsular rim 22, with a relatively small capsular opening 26, from encroaching onto the optic during fibrosis of capsular rim 22. As shown in FIG. 32, such projections 286 extend outwardly anteriorly from the plate haptic surface, and are disposed about and spaced from the optic. The projections extend outwardly no farther than the outer extent of the optic, typically to a height of about 1–1.5 mm. The projections may be in the form of continuous arcs (not shown) and may be inclined outwardly relative to the optic.

Figure 33:
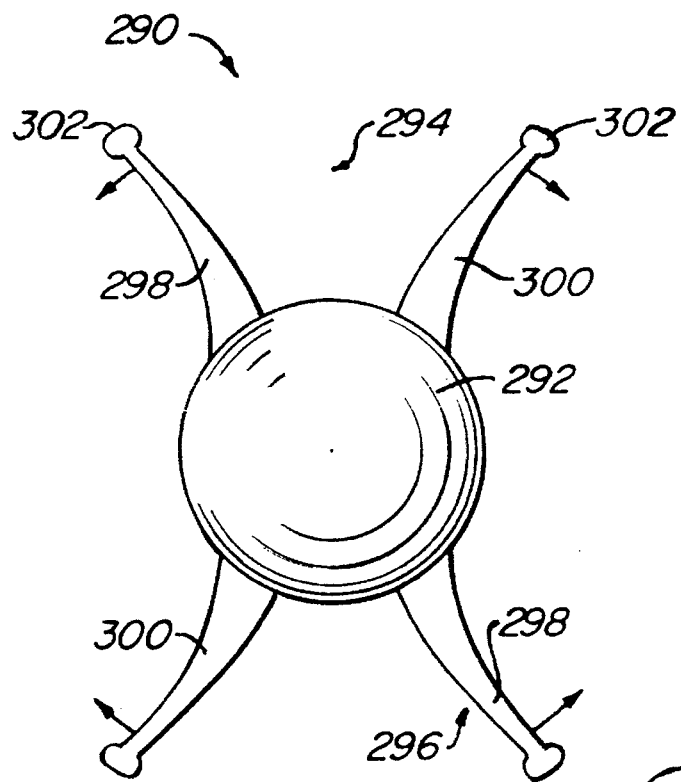

The modified accommodating intraocular lens 290 of FIG. 33 comprises a circular optic 292 and two pairs 294, 296 of curved, flexible haptics 298, 300 extending from opposite edges of the optic. These haptics have the form of relatively slender arms. At the outer ends of the haptics are enlarged knobs 302. The two haptics 298 of each haptic pair 294, 296 extend out from the optic 292 in mutually divergent relation and curve away from one another toward their outer ends, as shown. The four haptics are disposed in symmetrical relation relative to a plane of symmetry containing the axis of the optic and passing midway between the two haptics of each haptic pair. The two haptics 298 are located diametrically opposite one another, and the two haptics 300 are located diametrically opposite one another. The diametrical distance measured between the outer ends of the diametrically opposed haptics 298, 300 is made slightly greater than the maximum diameter of capsular bag 20. The lens 290 is implanted within the bag in much the same manner as the earlier embodiments of the invention and with the outer ends of the lens haptics 298,300 disposed between the anterior capsular rim 22 and posterior capsule 24 of the bag. The outer ends of the haptics press resiliently against the outer circumference of the bag and flex or bend in such a way as to both accommodate bags of different diameter and center the optic 292 behind the anterior capsulotomy in the bag. The anterior capsular rim 22 of the bag fibroses about the haptics to fixate the lens in the bag. After fibrosis is complete, brain initiated relaxation and constriction of the ciliary muscle 28 of the eye is effective to cause accommodation of the lens between near and distant vision positions in essentially the same manner as described earlier. During this accommodation, the lens buckles and the haptics flex anteriorly and posteriorly relative to the optic 292 in much the same way as described earlier. Fibrosis of the capsular rim about the haptic knobs 302 fixates the lens in the capsular bag and against dislocation in the event a tear or capsulotomy is formed in the posterior capsule 24 of the bag.

Figure 34:
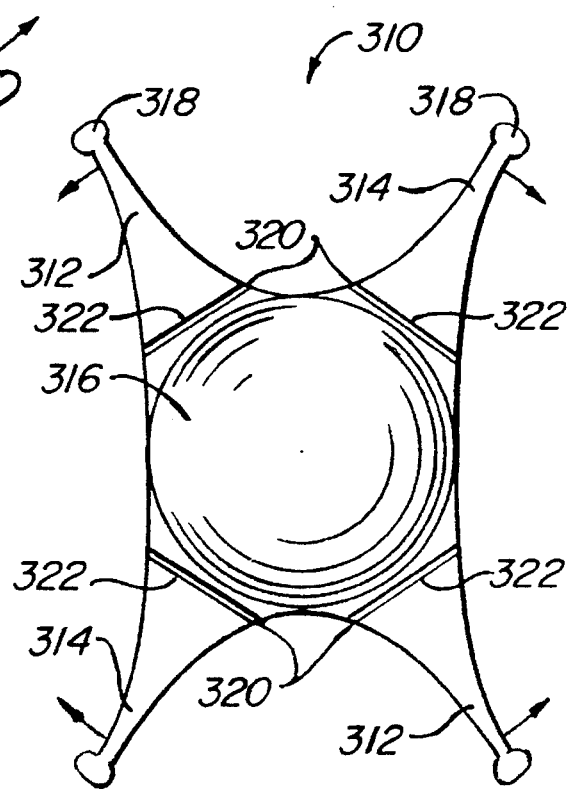

The modified accommodating intraocular lens 310 of FIG. 34 is similar to the lens 290 of FIG. 33 and differs from the lens 290 only in the following respects. The four haptics 312, 314 of the lens 310, rather than being slender curved arms like those of lens 290, are symmetrically tapered from relatively wide inner ends which are joined to the lens optic 316 to relatively narrow outer ends, At the outer ends of the haptics 312,314 are enlarged knobs 318. At inner ends of the haptics are grooves 320 which form flexible hinges 322 about which the haptics are flexible anteriorly and posteriorly of the optic. The diametrical distance between the outer ends of the diametrically opposed haptics 312, 314 approximates or slightly exceeds the maximum diameter of the capsular bag 20. The lens 310 is implanted within the bag, and fibrosis of the anterior capsular rim 22 of the bag occurs about the lens haptics in the same way as described in connection with lens 290. After fibrosis is complete, brain initiated relaxation and constriction of the ciliary muscle 28 of the eye cause accommodation of the lens in the same manner as described in connection with lens 290. Fibrosis of the capsular rim about the haptic knobs 318 fixates the lens in the capsular bag and against dislocation in the event a tear or capsulotomy is formed in the posterior capsule 24 of the bag.

The accommodating plate haptic lenses described to this point are referred to herein as simple plate haptic lenses. These lenses are intended for use when the capsulorhexis procedure performed on the eye is a properly performed continuous tear capsulotomy which provides an anterior annular capsular remnant or rim that remains intact and circumferentially continuous throughout fibrosis and has a sufficient radial width to retain the lens in the proper position within the capsular bag during and/or after fibrosis. According to another of its aspects, this invention provides modified accommodating intraocular lenses, illustrated in FIGS. 38–40 and 43–46 and referred to at plate haptic spring lenses, for use when the anterior capsular remnant or rim of the capsular bag is captured, that is cut or torn, or has too small a radial width to firmly retain the lens in proper position during and/or after fibrosis.

As noted earlier, a ruptured capsular remnant or rim may occur in different ways. For example, continuous tear circular capsulorhexis (FIG. 35) involves tearing the anterior capsule of the natural lens along a circular tear line to form in the anterior capsule a circular opening or capsulotomy 400 circumferentially surrounded by an annular remnant or rim 402 of the anterior capsule. Improper performance of this capsulorhexis can easily create slits or tears 404 in the capsular rim. A beer can or can opener capsulorhexis (FIG. 36) involves piercing the anterior capsule of the natural lens at a multiplicity of close positions 404 along a circular line and removing the circular portion of the anterior capsular rim within the pierced line to form an anterior capsulotomy 406 circumferentially surrounded by an annular rim 408. While this rim may be initially intact and circumferentially continuous, it has an inner scalloped edge 410 having stress-inducing regions that render the rim very prone to tearing radially, as shown at 411, during surgery or subsequent fibrosis. An envelope capsulorhexis (FIG. 37) involves slitting the anterior capsule of the natural lens along a horizontal line 412, then along vertical lines 414 extending upwardly from and intersecting the horizontal slit, and then tearing the anterior capsule along a tear line 416 which arches upwardly from the upper end of the vertical slit and then extends vertically downward to the horizontal slit. This capsulorhexis produces an anterior capsulotomy 418 bounded by a capsular remnant 420 which is slit at 412 and hence is inherently ruptured.

A ruptured anterior capsular remnant or rim may preclude utilization of a simple plate haptic lens of the invention for the following reasons. A ruptured rim may not firmly retain the lens haptics in the sulcus of the capsular bag during fibrosis. This renders the lens prone to decentration and/or dislocation, such as dislocation into the vitreous cavity if the posterior capsule tears or becomes cloudy over a period of time and is cut with a laser to provide a capsulotomy in the posterior capsule. A ruptured capsular rim may be incapable of assuming the taut trampoline-like condition of an intact capsular rim. As a consequence, a ruptured capsular rim may be incapable of effecting full posterior deflection of a plate haptic lens to a distant viewing position against the posterior capsule during and after fibrosis. A ruptured capsular rim may also permit anterior deflection of the lens during fibrosis. In either case, since the power of an intraocular lens is selected for each individual patient and may be dependent upon their spectacle power, and since good vision without glasses requires the lens optic to be situated at precisely the correct distance from the retina throughout the range of accommodation, a simple plate haptic lens of the invention may not be acceptable for use with a ruptured anterior capsular remnant or rim.

Figure 35:
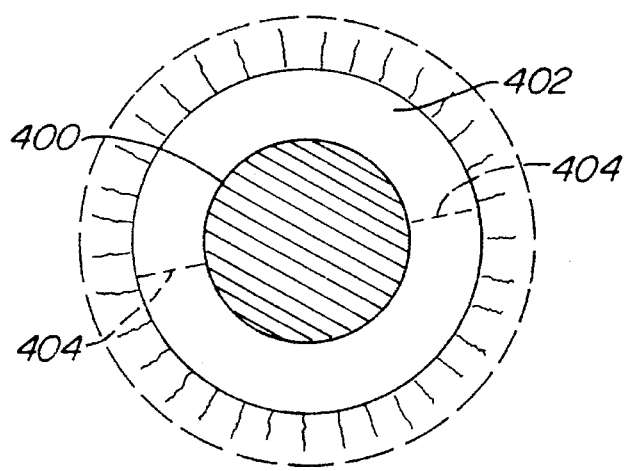
FIGS. 35–37 illustrate the capsulotomy produced by a continuous tear circular capsulotomy, a beer can capsulotomy, and an envelope capsulotomy, respectively.
Figure 36:
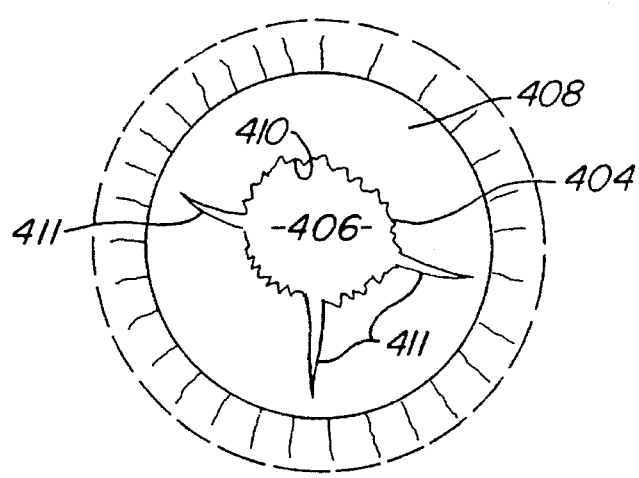
Figure 37:
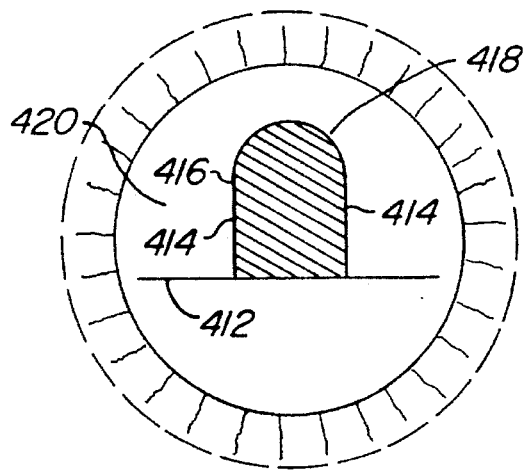
Figure 38:
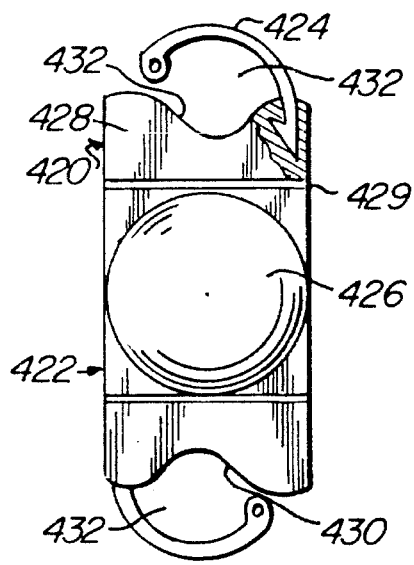
FIG. 38 is an anterior face view of a plate haptic spring lens according to the invention.
Figure 39:
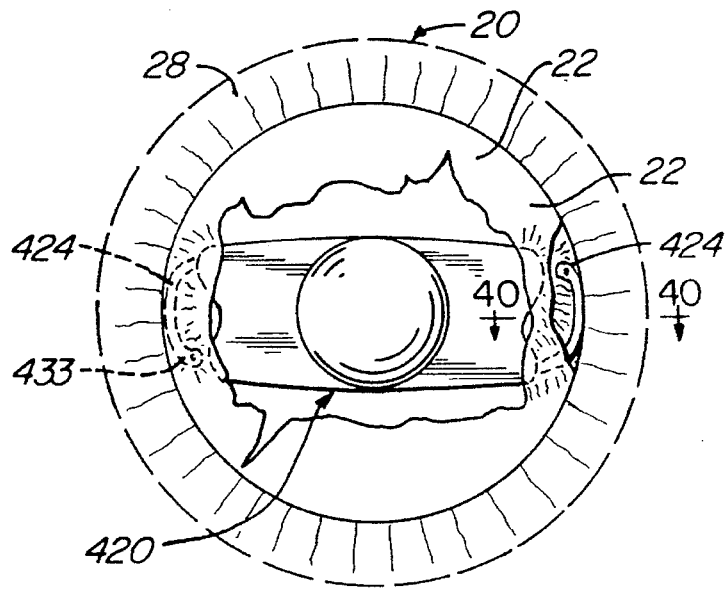
FIG. 39 is a view similar to FIG. 4 showing the plate haptic spring lens of FIG. 38 implanted within the eye.
Figure 40:
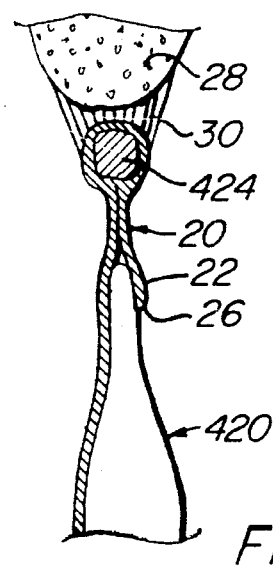
FIG. 40 is an enlarged section taken on line 40—40 in FIG. 39.

FIGS. 38–40 illustrate an accommodating plate haptic spring intraocular lens 420 of the invention for use with a ruptured anterior capsular remnant or rim, such as any one of those illustrated in FIGS. 35–37. This plate haptic spring lens has a lens body 422 proper similar to that of the plate haptic lens 32 in FIGS. 1–8 and springs 424 at the ends of the body. The lens body 422 includes a central optic 426 and flexible plate haptics 428 extending outward from diametrically opposite sides of the optic. These haptics are joined to the optic by hinges 429 formed by grooves in the anterior side of the lens. The springs 424 are resilient loops which are staked at one end to the ends of the haptics 428 at opposite sides of the longitudinal centerline of the body. These spring loops bow outwardly lengthwise of the lens body from their staked ends to their centers and then turn back toward the lens body from their centers to their free ends. The ends of the haptics 428 have recesses 430 over which the spring loops extend in such a way that the loops and the edges of the recesses form openings 432 therebetween. The ends of the spring loops have holes 433 to receive instruments for positioning the lens in the eye.

The plate haptic spring lens 420 is implanted within the capsular bag 20 of the eye in the same manner as described earlier in connection with the simple plate haptic lenses of the invention. That is to say, the lens 420 is implanted within the eye while its ciliary muscle 28 is paralyzed in its relaxed state, and the capsular bag thereby stretched to its maximum diameter (9–11 mm). The overall length of the lens body 422 measured between the ends of the lens haptics 428 at either side of the haptic recesses 430 substantially equals the inner diameter of the stretched capsular bag. The overall length of the lens measured between the outer edges of the spring loops 424 at their centers when the loops are in their normal unstressed state is slightly greater than this inner diameter of the stretched capsular bag. For example, if the inner diameter of the stretched capsular bag is in the range 10–10.6 mm, the lens body 422 will have an overall length of 10–10.6 mm measured between the outer ends of the lens haptics, and the overall length of the lens measured between the centers of the unstressed spring loops will be in the range of 11–12.5 min.

FIGS. 39 and 40 illustrate the plate haptic spring lens 420 implanted in a capsular bag 20 which is stretched by relaxation of the ciliary muscle 28 and has a torn anterior capsular rim 22 such as might result from an improperly performed continuous tear circular capsulorhexis. Because the rim is torn, the lens body 422 will not fit as snugly in the stretched bag as it would if the capsular rim were an intact rim free of tears. The haptic spring loops 424, however, press outward against the wall of the capsular bag sulcus about the rim of the bag to fixate the lens in the bag during fibrosis following surgery. Fibrosis of the torn capsular rim 22 occurs about the outer ends of the plate haptics 428, about the spring loops 424, and through the openings 432 between the loops and the ends of the haptics in such a way as to effect fusion of the torn rim, or more precisely the remnants of the torn rim, to the posterior capsule 24 of the capsular bag. The outer ends of the haptics and the spring loops are thereby shrink-wrapped by fibrosis in somewhat the same manner as explained earlier in connection with the simple plate haptic lenses of the invention. Even though the torn capsular rim 22 may be incapable of stretching to the taut trampoline condition discussed earlier when the ciliary muscle is relaxed, this shrink-wrapping of the lens during fibrosis of the torn rim will firmly fixate the lens in the capsular bag and should cause some posterior deflection of the lens against the elastic posterior capsule 24. Accordingly, brain-induced constriction and relaxation of the ciliary muscle 28 after fibrosis of the torn capsular rim is complete should effect accommodation of the plate haptic spring lens in much the same way, but possibly not with the same amount of accommodation, as the simple plate haptic lens with an intact non-ruptured capsular rim.

While the plate haptic spring lens 420 is designed for use with a ruptured anterior capsular remnant or rim, it can also be utilized with an intact rim. A plate haptic spring lens also compensates for improper lens placement in the eye with one end of the lens situated in the capsular bag and the other end of the lens situated in the ciliary sulcus of the eye since the spring loops will expand outwardly to engage both the inner edge of the bag and the wall of the ciliary sulcus. In this regard, an advantage of the plate haptic spring lenses of the invention over the simple plate haptic lenses resides in the fact-that the spring lenses eliminate the need to have on hand in the operating room both a simple plate haptic lens for use with an intact capsular rim and a plate haptic spring lens as a backup for the plate haptic lens in the event the rim is ruptured during surgery.

Another advantage of the haptic spring lens 420 resides in the fact that it permits the lens to have a larger optic than a simple plate haptic lens whose optic diameters will normally be within the range of 4-7 mm. Thus, since the haptic spring lens relies on the spring loops 424 rather than on the capsular remnant or rim 22 to retain the lens in position during fibrosis, the lens may be used with a capsular remnant or rim of smaller radial width and hence larger capsulotomy diameter than those required for use of the simple plate haptic accommodating lenses. The larger capsulotomy, of course, permits a larger optic diameter in the range of 7–9 mm which offers certain ophthalmological benefits.

Figure 41:
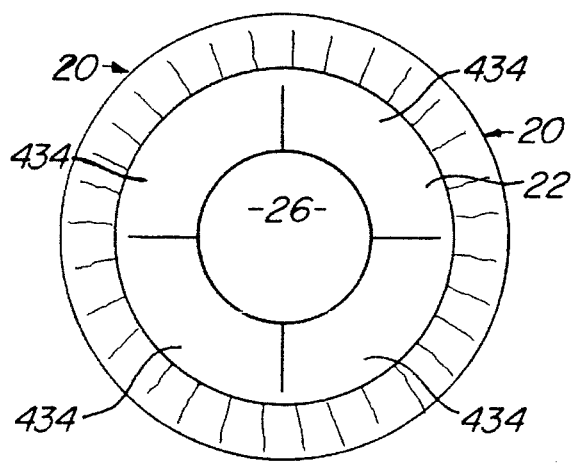
FIGS. 41 and 42 illustrate two ways of enlarging the capsulotomy of a capsular bag after completion of fibrosis to allow anterior movement of a relatively large lens optic.
Figure 42:
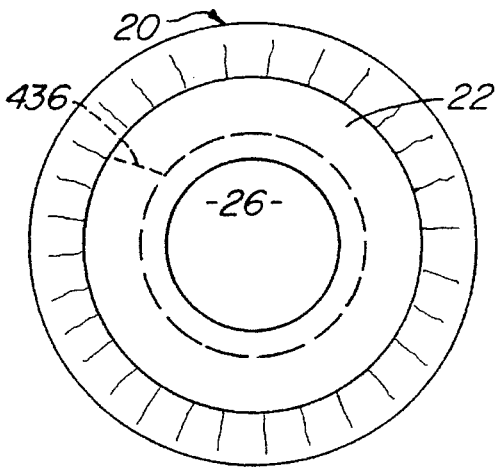

The large capsulotomy necessary to accommodate a large optic spring accommodating lens may be formed during the original surgery by a planned large continuous tear circular capsulorhexis, a beer can capsulorhexis of the desired large diameter, a planned envelope capsulotomy or the cutting of radial slits into a small continuous tear capsulotomy during surgery after implanting the spring accommodating lens. According to another of its aspects, the invention provides a method whereby the desired large anterior capsulotomy may be formed after the original surgery following completion of fibrosis. This method involves slitting an annular capsular rim radially with a laser after fibrosis is complete into a number of flap-like remnants 434 (FIG. 41) which are easily displaced by the lens during accommodation to enlarge the capsulotomy sufficiently to permit the lens optic to pass through the capsulotomy. Alternatively, the capsulotomy may be enlarged by cutting the capsular rim with a laser circumferentially along a circular line 436 (FIG. 42) concentric with and radially outwardly of the original edge of the capsulotomy to enlarge the latter.

Figure 43:
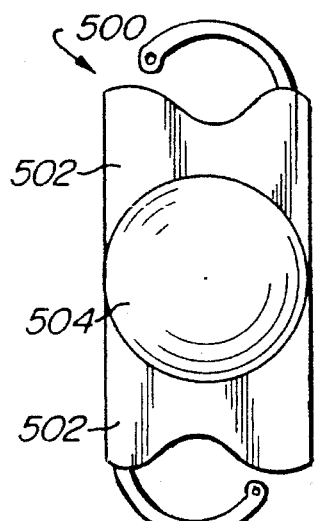
FIG. 43 is an anterior side view of a modified plate haptic lens according to the invention.
Figure 44:
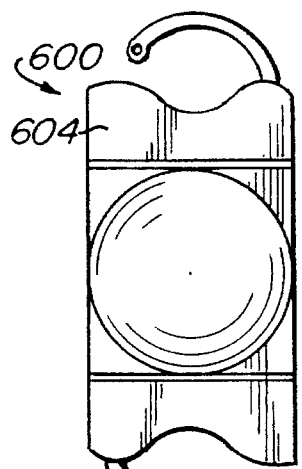
FIGS. 44–46 illustrate modified plate haptic spring lenses according to the invention.
Figure 45:
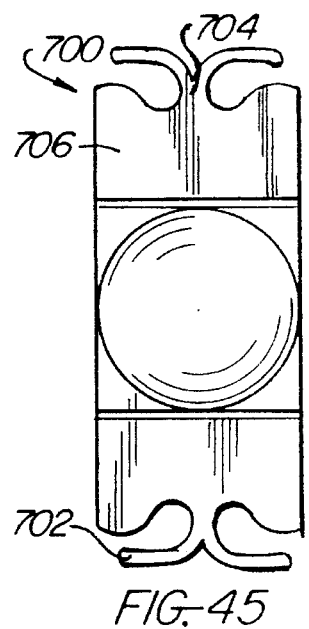
Figure 46:
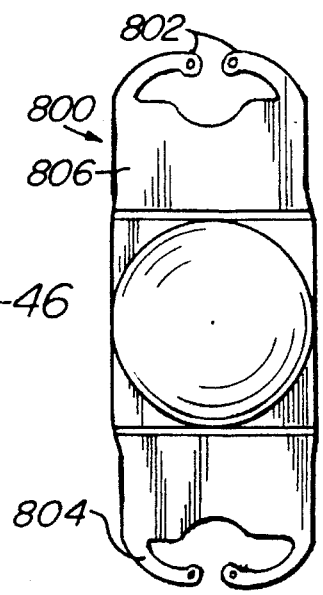

The modified plate haptic spring lens 500 of FIG. 43 is identical to the lens 420 just described except that the haptics 502 of the modified lens, rather than being hinged to the lens optic 504, are resiliently flexible throughout their length like those of the plate haptic lens in FIG. 9. FIG. 44 illustrates a further modified plate haptic spring lens 600 according to the invention which is identical to the lens 420 except that the spring loops 602 of the modified lens are formed integrally with the lens haptics 604. The modified lens 700 and 800 of FIGS. 45 and 46 are identical to the lens 600 except that the modified lenses have a pair of spring loops at each end. The spring loops 702 of lens 700 have common base portions 704 integrally joined to the ends of the lens haptics 706 along the longitudinal centerline of the lens and free ends which curve outwardly from the base portions both endwise and laterally of the lens. The spring loops 802 of lens 800 have base portions 804 integrally joined to the ends of the lens haptics 806 along the longitudinal edges of the haptics and opposite free ends which curve inwardly toward one another laterally of the lens.

Thus there has been shown and described a novel accommodating intraocular lens which fulfills all the objects and advantages sought therefor. Many changes, modifications, variations and other uses and applications of the subject invention will, however, become apparent to those skilled in the art after considering this specification together with the accompanying drawings and claims. All such changes, modifications, variations and other uses and applications which do not depart from the spirit and scope of the invention are deemed to be covered by the invention which is limited only by the claims which follow.

The inventor claims:

1. An ophthalmic method for providing accommodating vision to a human eye having a natural capsular bag attached about its perimeter to the ciliary muscle of the eye and from which the natural lens matrix has been removed, the bag including an elastic posterior capsule urged anteriorly by vitreous pressure in the eye, and an anterior capsulotomy circumferentially surrounded by a capsular remnant having epithelial cells on its posterior side which cause fusion of the remnant to the posterior capsule by fibrosis during a certain postoperative period following surgery, said method comprising the steps of:

providing an intraocular lens having normally anterior and posterior sides and including a central optic, and plate haptics extending from opposite edges of the optic and having inner ends joined to the optic and opposite outer ends movable anteriorly and posteriorly relative to said optic, paralyzing the ciliary muscle to place the muscle in its relaxed state, while the ciliary muscle is paralyzed in its relaxed state, implanting said intraocular lens within said capsular bag in a position wherein the outer ends of said haptics are disposed between said capsular remnant and the outer perimeter of said posterior capsule and said optic is aligned with said capsulotomy, and maintaining the ciliary muscle in its relaxed state during said postoperative period in a manner such that fibrosis occurs about said haptics and the haptics form pockets in the fibrose tissue, and after completion of fibrosis, relaxation of the ciliary muscle causes posterior deflection of the implanted lens and constriction of the ciliary muscle causes anterior accommodation of the implanted lens.

2. An ophthalmic method according to claim 1 wherein:

paralyzing the ciliary muscle stretches the capsular bag to its maximum diameter and stretches said capsular remnant to a relatively taut condition, fibrosis produces shrinkage off said capsular remnant, opposing endwise compression forces of said lens haptics, and posterior deflection of said implanted lens by said compression forces and said capsular remnant to a distant vison position wherein the implanted lens presses rearwardly against said posterior capsule and stretches the posterior capsule rearwardly to produce an anterior bias force on the implanted lens, relaxation of the ciliary muscle after fibrosis is complete reduces said vitreous pressure and causes posterior movement of said implanted lens to said distant vision position by the capsular rim, and constriction of the ciliary muscle after fibrosis is complete increases said vitreous pressure, relaxes said capsular remnant, and causes anterior accommodation of the implanted lens by vitreous pressure and said bias force.

3. An ophthalmic method according to claim 1 wherein:

said lens includes hinges joining the inner ends of said haptics to said optic and about which said haptics are pivotally movable anteriorly and posteriorly relative to said optic.

4. An ophthalmic method according to claim 3 wherein:

said hinges are flexible portions of said lens.

5. An ophthalmic method according to claim 3 wherein:

said intraocular lens contains grooves in at least one of said lens sides along the inner ends of said haptics forming flexible, reduced thickness portions of the intraocular lens which constitute said hinges.

6. An ophthalmic method according to claim 1 wherein:

said haptics are flexible throughout their length in said anterior and posterior directions relative to said optic.

7. An ophthalmic method according to claim 1 wherein:

said lens includes fixation means at the outer ends of said haptics around which fibrosis of said capsular rim occurs to fix said lens in the capsular bag.

8. An ophthalmic method according to claim 7 wherein:

said fixation means and haptics are separable to permit removal of said lens from and replacement of said lens in said capsular bag.

9. An ophthalmic method according to claim 1 wherein:

said intraocular lens includes springs at the outer ends of said haptics having normal unstressed positions wherein said springs extend beyond their adjacent outer haptic ends in the endwise directions of the haptics for resilient engagement with the perimeter of said bag to firmly position the lens in the bag in the event that said capsular remnant is torn, split, or otherwise ruptured during surgery or fibrosis.

10. An ophthalmic method according to claim 9 wherein:

said springs comprise spring loops.

11. An ophthalmic method according to claim 9 wherein:

said springs comprise spring loops.

12. An ophthalmic method according to claim 1 wherein:

said intraocular lens includes fixation means at the outer ends of said haptics about which fibrosis occurs to positively fix the intraocular lens in the capsular bag, the optic of said intraocular lens is larger than said capsulotomy, and said method includes the additional step of cutting said capsular remnant about said capsulotomy after completion of fibrosis in such a way as to permit free movement of said optic into and from the capsulotomy during accommodation.

13. An ophthalmic method according to claim 12 wherein:

said additional step involves slitting said capsular remnant outwardly from the edge of said capsulotomy.

14. An ophthalmic method according to claim 12 wherein:

said additional step involves cutting said capsular remnant circumferentially about said capsulotomy to enlarge the capsulotomy.

15. An ophthalmic method of correcting the vision of a patient's eye having a natural lens including anterior and posterior capsules and containing a natural lens matrix, comprising the steps of:

removing the natural lens matrix from said natural lens by a surgical procedure involving anterior capsulorhexis of the lens to provide in the eye a natural lens bag including an anterior capsulotomy circumferentially surrounded by a capsular remnant having epithelial cells on its posterior side which cause fusion of the remnant to the posterior capsule by fibrosis during a certain postoperative period following surgery, providing an intraocular lens having normally anterior and posterior sides and including a central optic, and plate haptics extending from two diametrically opposite edges of the optic having inner ends joined to the optic and opposite outer ends movable anteriorly and posteriorly relative to said optic, implanting said intraocular lens within said capsular bag while the ciliary muscle is paralyzed in its relaxed state and in an implanted position wherein the outer ends of said haptics are disposed between said capsular remnant and the outer perimeter of said posterior capsule and said optic is aligned with said capsulotomy, and maintaining the ciliary muscle in its relaxed state during said post operative period in a manner such that fibrosis occurs about said haptics and said haptics form pockets in the fibrose tissue, and after completion of fibrosis, relaxation of the ciliary muscle causes posterior deflection of the implanted lens, and constriction of the ciliary muscle causes anterior accommodation of the implanted lens.

16. An ophthalmic method according to claim 15 wherein:

paralyzing the ciliary muscle stretches the capsular bag to its maximum diameter and stretches said capsular remnant to a relatively taut condition, fibrosis produces shrinkage of said capsular remnant, opposing endwise compression forces on said lens haptics, and posterior deflection of said lens by said compression forces and said capsular remnant to a distant vison position wherein the lens presses rearwardly against said posterior capsule and stretches the posterior capsule rearwardly to produce an anterior bias force on the lens, relaxation of the ciliary muscle after fibrosis is complete reduces said vitreous pressure and causes posterior movement of said lens to said distant vision position by the capsular rim, and constriction of the ciliary muscle after fibrosis is complete increases said vitreous pressure, relaxes said capsular remnant, and causes anterior accommodation of the lens by vitreous pressure and said bias force.

17. An ophthalmic method according to claim 15 wherein:

said intraocular lens includes hinges joining the inner ends of said haptics to said optic and about which said haptics are pivotally movable anteriorly and posteriorly relative to said optic.

18. An ophthalmic method according to claim 17 wherein:

said hinges are flexible portions of said lens.

19. An ophthalmic method according to claim 17 wherein:

said intraocular lens contains grooves in one of said lens sides along the inner ends of said haptics forming flexible, reduced thickness portions of the lens which constitute said hinges.

20. An ophthalmic method according to claim 15 wherein:

said haptics are flexible throughout their length in said anterior and posterior directions relative to said optic.

21. An ophthalmic method according to claim 15 wherein:

said intraocular lens includes fixation means at the outer ends of said haptics around which fibrosis of said capsular rim occurs to fix said intraocular lens in the capsular bag.

22. An ophthalmic method according to claim 21 wherein:

said fixation means and haptics are separable to permit removal of said lens from and replacement of said lens in said capsular bag.

23. An ophthalmic method according to claim 15 wherein:

said intraocular lens includes springs at the outer ends of said haptics having normal unstressed positions wherein said springs extend beyond their adjacent outer haptic ends in the endwise directions of the haptics for resilient engagement with the perimeter of said bag to firmly position the lens in the bag in the event that said capsular remnant is torn, split, or otherwise ruptured during surgery or fibrosis.

24. An ophthalmic method according to claim 15 wherein:

said intraocular lens includes fixation means at the outer ends of said haptics about which fibrosis occurs to positively fix the intraocular lens in the capsular bag, the optic of said intraocular lens is larger than said capsulotomy, and said method includes the additional step of cutting said capsular remnant about said capsulotomy after completion of fibrosis in such a way as to permit free movement of said optic into and from the capsulotomy during accommodation.

25. An ophthalmic method according to claim 24 wherein:

said additional step involves slitting said capsular remnant outwardly from the edge of said capsulotomy.

26. An ophthalmic method according to claim 24 wherein:

said additional step involves cutting said capsular remnant circumferentially about said capsulotomy to enlarge the capsulotomy.

* * * * *